US007105653B2

(12) United States Patent
Shanafelt et al.

(10) Patent No.: US 7,105,653 B2
(45) Date of Patent: *Sep. 12, 2006

(54) IL-2 SELECTIVE AGONISTS AND ANTAGONISTS

(76) Inventors: Armen B. Shanafelt, 355 Arbor Dr., Carmel, IN (US) 46032; Jeffrey M. Greve, 1066 Park Hills Rd., Berkeley, CA (US) 94708; Gary Jesmok, 485 Carlston St., Richmond, CA (US) 94805; Kenneth Lembach, 662 Park Hill Rd., Danville, CA (US) 94526; Gayle D. Wetzel, 971 Center Ave., Martinez, CA (US) 94553

( * ) Notice: Subject to any disclaimer, the term of this patent is extended or adjusted under 35 U.S.C. 154(b) by 171 days.

This patent is subject to a terminal disclaimer.

(21) Appl. No.: 10/826,809

(22) Filed: Apr. 17, 2004

(65) Prior Publication Data

US 2004/0175357 A1    Sep. 9, 2004

Related U.S. Application Data

(60) Division of application No. 09/341,351, filed on May 13, 1999, now Pat. No. 6,955,807, which is a continuation-in-part of application No. 09/080,080, filed on May 15, 1998, now abandoned.

(60) Provisional application No. 60/160,077, filed on May 15, 1998.

(51) Int. Cl.
*C12N 5/10* (2006.01)
*C12N 15/26* (2006.01)
*C12N 15/63* (2006.01)

(52) U.S. Cl. .................. 536/23.5; 435/71.1; 435/71.2; 435/252.3; 435/320.1; 435/69.52

(58) Field of Classification Search ..................... None
See application file for complete search history.

(56) References Cited

U.S. PATENT DOCUMENTS

| | | | | |
|---|---|---|---|---|
| 4,518,584 A | 5/1985 | Mark et al. | ..................... | 424/85 |
| 4,588,585 A | 5/1986 | Mark et al. | ..................... | 424/85 |
| 4,853,332 A | 8/1989 | Mark et al. | ............ | 435/252.33 |
| 4,959,314 A | 9/1990 | Mark et al. | ................. | 435/69.1 |
| 5,116,943 A | 5/1992 | Koths et al. | ................. | 530/351 |
| 5,206,344 A | 4/1993 | Katre et al. | ................. | 530/351 |
| 5,229,109 A | 7/1993 | Grimm et al. | ............. | 424/85.2 |
| 5,696,234 A | 12/1997 | Zurawski et al. | ........... | 530/351 |

FOREIGN PATENT DOCUMENTS

| | | |
|---|---|---|
| EP | 0119621 | 9/1984 |
| EP | 0163249 | 12/1985 |
| EP | 0267795 | 5/1988 |
| WO | 8904665 | 6/1989 |
| WO | 9606860 | 3/1996 |
| WO | 9731622 | 9/1997 |
| WO | 9741232 | 11/1997 |

OTHER PUBLICATIONS

Zurawski S.M. and Zurawski G., Receptor antagonist and selective agonist derivatives of mouse interleukin-2, Embo.J., 11(11): 3905-3910 (1992).
Zurawski et al., Definition and spatial location of mouse interleukin-2 residues that interact with its heterotrimeric receptor, Embo.J., 12(13): 5113-5119 (1993).
Thèze et al., Interleukin 2 and its receptors: recent advances and new immunological functions, Immunol. Today, 17(10): 481-486 (1996).
Xu et al., Biological and receptor-binding activities of human interleukin-2 mutated at residues 20Asp, 125Cys or 127Ser, Eur. Cytokine Netw., 6(4): 237-244 (1995).
Jacobson et al., Rational interleukin 2 therapy for HIV positive individuals: Daily low doses enhance immune function without toxicity, Proc.Natl.Sci., 93: 10405-10410 (1996).
Smith K. A., Lowest Dose Interleukin-2 Immunotherapy, Blood, 81(6): 1414-1423 (1993).
Kaplan et al., Rational Immunotherapy with Interleukin 2, Biotech., 10(2): 157-162 (1992).
Buchli et al., Structural and Biologic Properties of a Human Aspartic Acid-126 Interleukin-2 Analog, Arch.Biochem. Biophys., 307(2): 411-415 (1993).
Cellular and Molecular Immunology, Abbas et al., eds., 1997, W.B. Saunders Company, Chapter 12, Cytokines, pp. 250-267.
Immunology, Roitt et al., eds., 1996, pp. 8.8-8.16, Fourth Edition, Mosby.
Zurawski, S.M. and Zurawski, G., Mouse interleukin-2 structure-function studies: substitutions in the first α-helix can specificaly inactivate p70 receptor binding and mutations in the fifth α-helix can specifically inactivate p55 receptor binding, Embo.J., 8(9): 2583-2590 (1989).
Zurawski et al., Partial agonist/antagonist mouse interleukin-2 proteins indicate that a third component of the receptor complex functions in signal transduction, Embo.J., 9(12):3899-3905 (1990).
Zurawski, G., Analysing lymphokine-receptor interactions of IL-1 and IL-2 by recombinant-DNA technology, Trends Biotech., 9: 250-257 (1991).

*Primary Examiner*—Prema Mertz
(74) *Attorney, Agent, or Firm*—John W. Mahoney

(57) ABSTRACT

The invention is directed to a polypeptide comprising a human IL-2 mutein numbered in accordance with wild-type IL-2 wherein said human IL-2 is substituted at at least one of positions 20, 88 or 126, whereby said mutein preferentially activates T cells over NK cells. D20H and I, N88G, I, and R, in particular have a relative T cell-differential activity much greater than native IL-2, with predicted associated reduced in vivo toxicity. The invention also includes polynucleotides coding for the muteins of the invention, vectors containing the polynucleotides, transformed host cells, pharmaceutical compositions comprising the muteins, and therapeutic methods of treatment.

3 Claims, 20 Drawing Sheets

IL-2 SELECTIVE AGONISTS AND ANTAGONISTS

CROSS REFERENCE TO RELATED APPLICATIONS

Figure 1A:
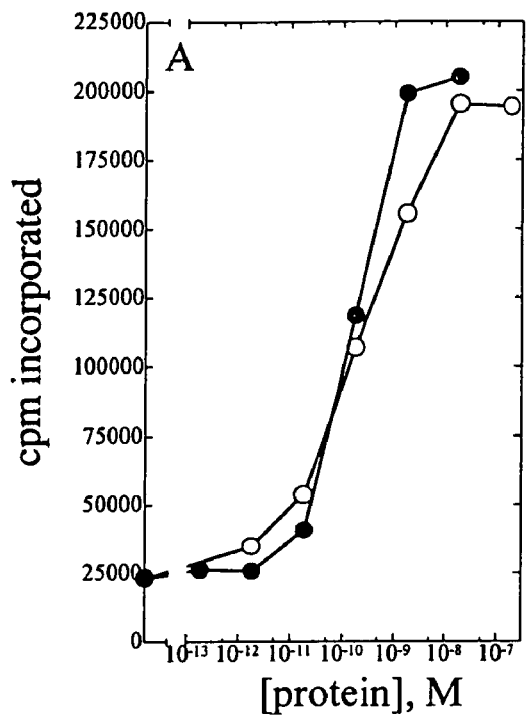
Figure 1B:
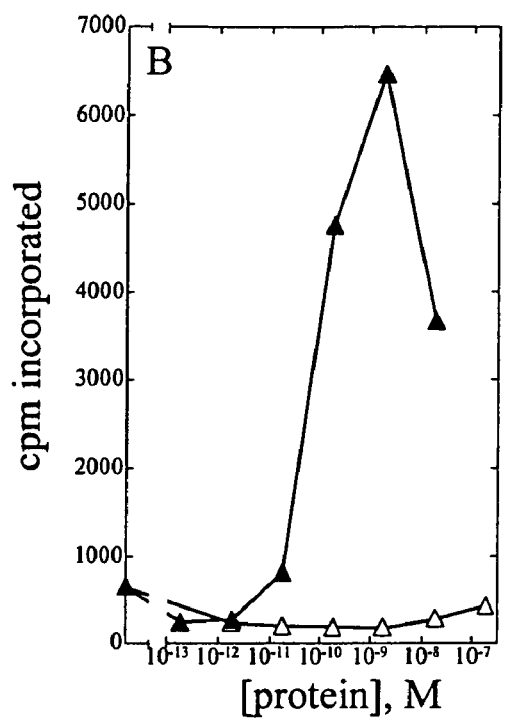
Figure 2A:
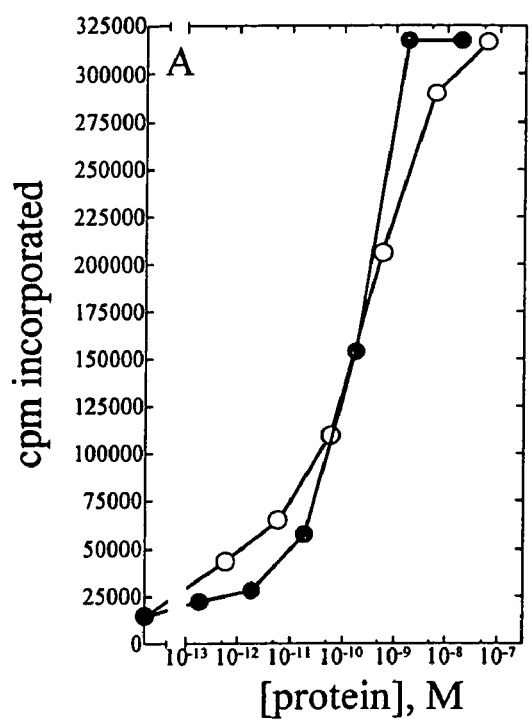
Figure 2B:
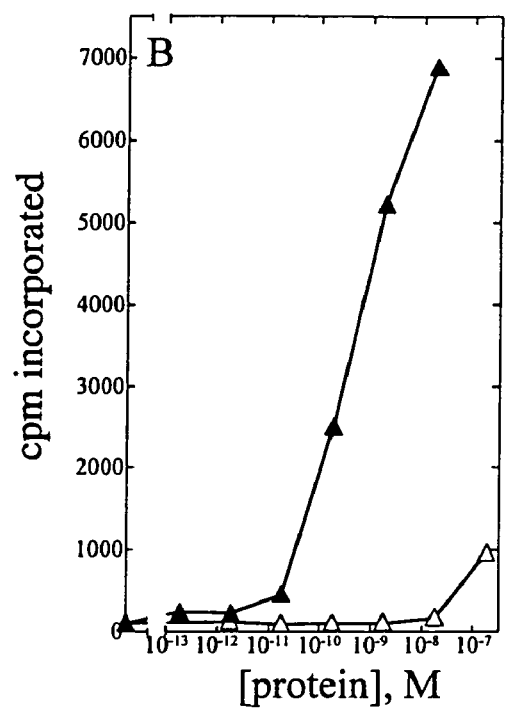
Figures 3A, 3B:
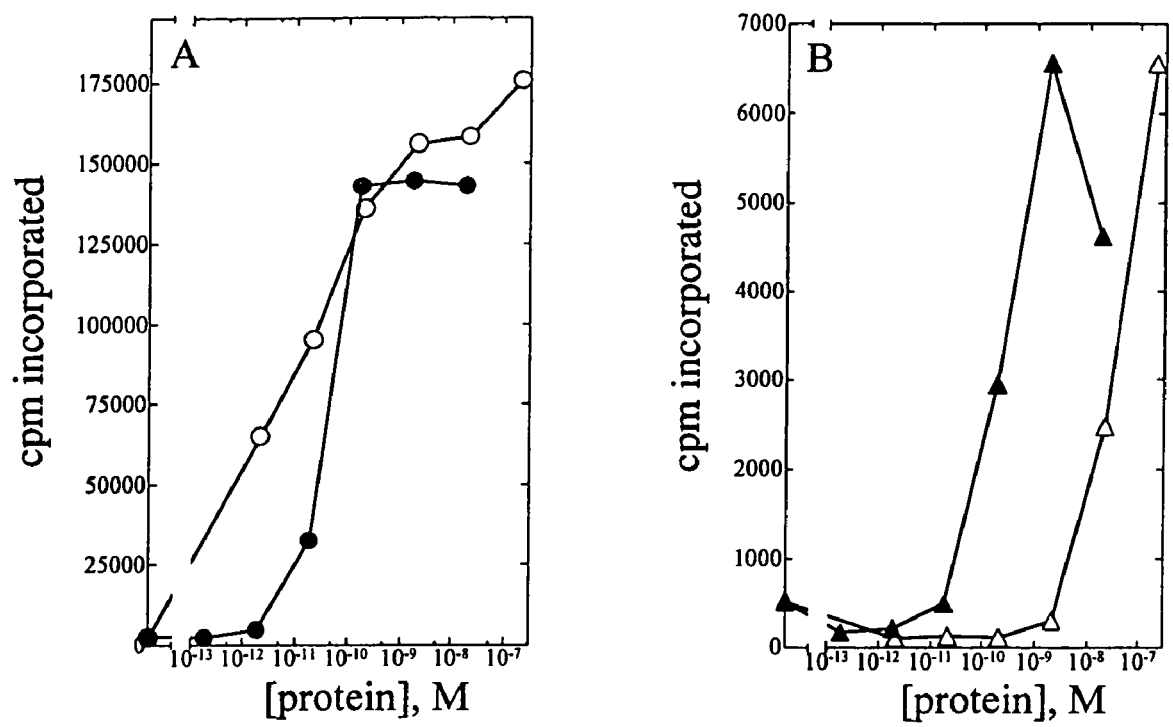
Figure 4A:
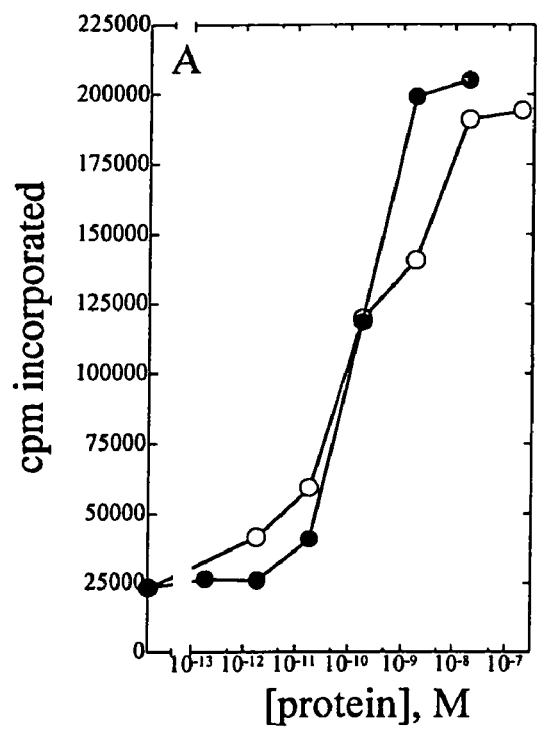
Figure 4B:
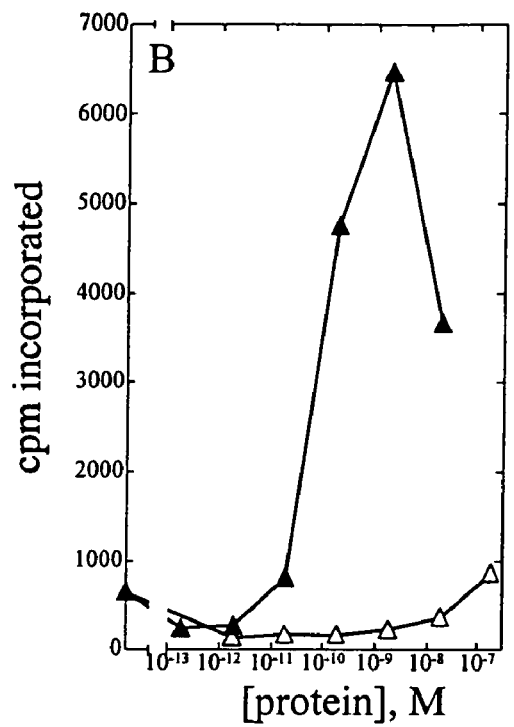
Figure 5A:
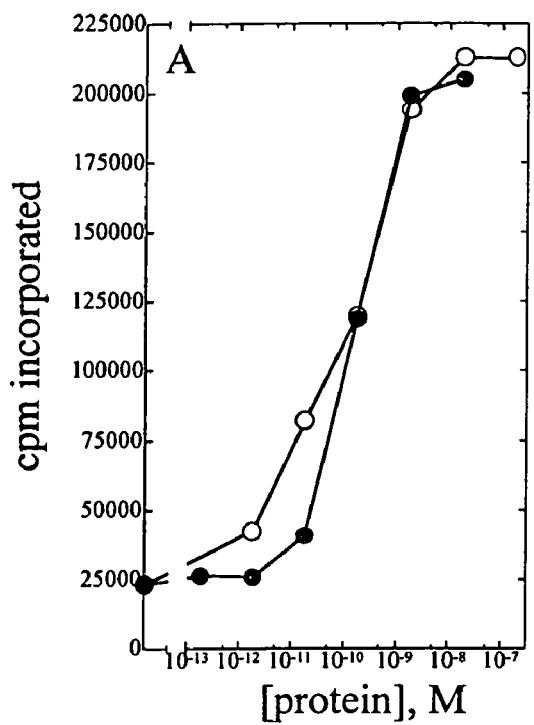
Figure 5B:
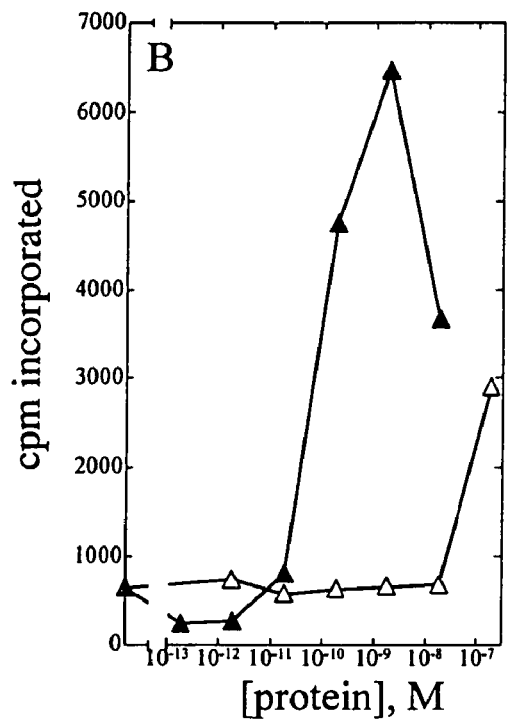
Figure 6A:
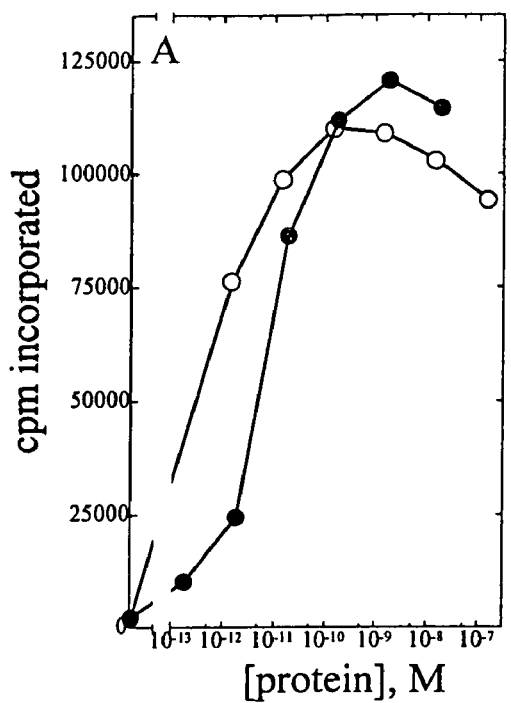
Figure 6B:
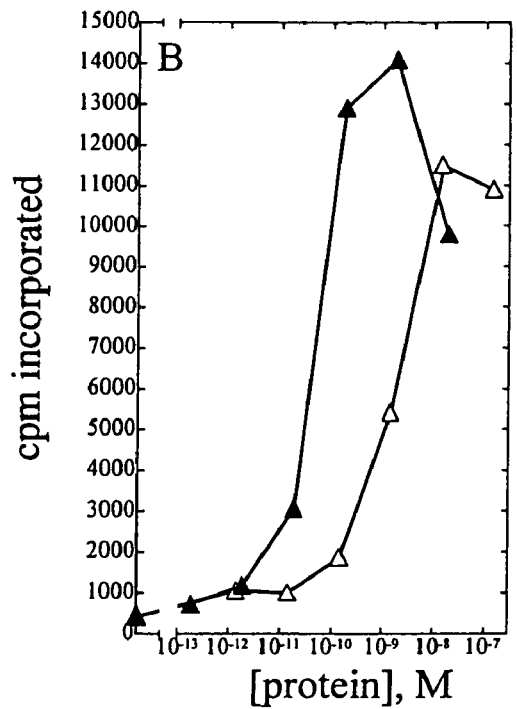
Figure 7A:
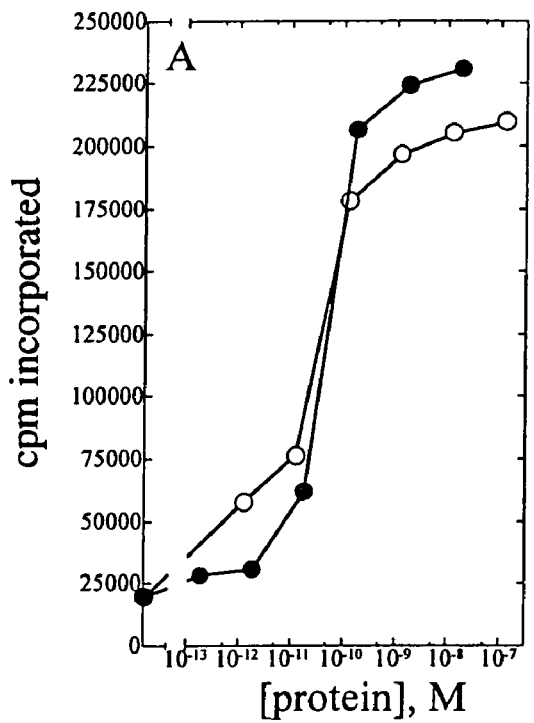
Figure 7B:
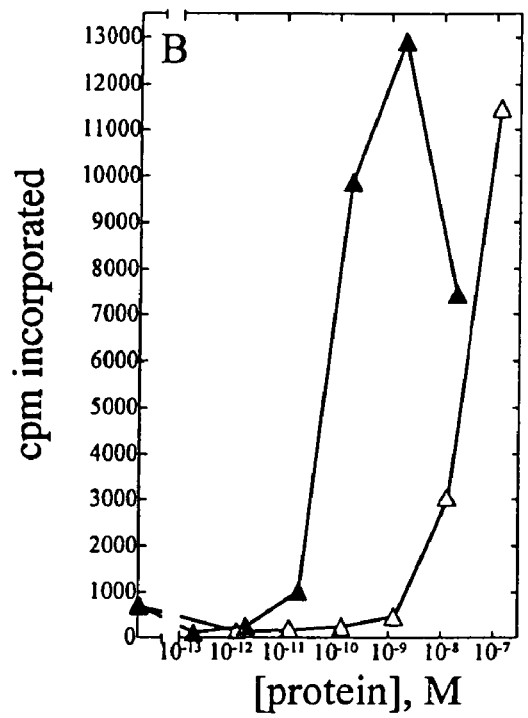

This application is a divisional of U.S. Ser. No. 09/341,351, filed May 13, 1999, now U.S. Pat. No. 6,955,807 which is a continuation-in-part application of U.S. Ser. No. 09/080,080 filed May 15, 1998 now abandoned.

BACKGROUND

1. Field of the Invention

The invention is generally related to the fields of pharmacology and immunology. More specifically, the invention is directed to novel compositions of matter for selectively activating T cells (PHA-blasts), and having reduced activation of Natural Killer ("NK") cells. The novel compositions include variants of the cytokine family, and in particular human Interleukin-2 ("IL-2").

2. Description of Related Art

Interleukin 2 (IL-2) is a potent immune stimulator, activating diverse cells of the immune system, including T cells, B cells, and monocytes. IL-2 is also a potent and critical growth factor of T cells. It was by virtue of these activities that IL-2 was tested for its ability to treat cancer. Human IL-2 is an-FDA approved drug for the treatment of metastatic renal carcinoma and metastatic melanoma. The use of IL-2 in eligible patients is restricted due to the severe toxicity associated with IL-2 therapy; it is estimated that at best only 20% of eligible patients actually receive therapy. The toxicities associated with IL-2 therapy include severe fever, nausea, vomiting, vascular leak and serious hypotension. Despite these toxicities, however, IL-2 is effective for its approved indications (~17% objective response rate).

Although the structure/function analysis of mouse IL-2 has been extensive (Zurawski, S. M. and Zurawski, G. (1989) Embo J 8: 2583–90; Zurawski, S. M, et. al., (1990) Embo J 9: 3899–905; Zurawski, G. (1991). Trends Biotechnol 9: 250–7; Zurawski, S. M. and Zurawski, G. (1992) Embo J 11: 3905–10. Zurawski, et.al., EMBO J, 12 5113–5119 (1993)), only limited analysis of human IL-2 has occurred. Most studies with human IL-2 muteins have been performed on murine cells; however, limited studies have occurred using human PHA-blasts, which express the high affinity IL-2 receptor IL-2Rαβγ. The studies using PHA-blasts confirmed the importance of the residues Asp-20 and the D-helix of human IL-2. It has been shown that position Asp-20 and Gln-126 of human IL-2 are the primary residues responsible for interaction with the IL-2 receptor β- and γ-subunits, respectively (reviewed in Thèze, et. al., Immunol. Today, 17, 481–486 (1996)) Although residues in the C-helix of mouse IL-2 have been shown to be involved in interaction with mouse IL-2Rβ (Zurawski, et.al., EMBO J, 12 5113–5119 (1993)), the equivalent residues in human IL-2 have not been shown to have the same properties (these residues in human IL-2 would be Asp-84 and Asn-88). Because significant species specificity is shown between human and mouse IL-2 (human IL-2 exhibits ~100-fold reduced activity in murine systems), it is difficult to predict whether the same type of interactions are occurring within species boundaries. No studies are known using cells expressing only the human intermediate affinity receptor IL-2Rβγ.

Some human IL-2 muteins have been examined for their activity on human PHA blasts (Xu, et. al., Eur. Cytokine Netw, 6, 237–244 (1995)). Muteins containing substitutions of Asp-20 with Leucine (D20L), as well as Arginine, Asparagine, and Lysine, were shown to have severe defects in their ability to induce proliferation of PHA-blasts. Thus, this art teaches that substitution of Asp-20 will result in muteins of compromised activity. Additionally, Xu, et al states that to date (1995) no useful IL-2 muteins have been identified for either clinical or research applications.

The human IL-2 Q126D mutein generated by Buchli and Ciardelli, Arch. Biochem. Biophys, 307(2): 411–415, (1993) showed significantly compromised activity in both potency and agonism; in human T cell assays, it exhibited ~1,000-fold less activity than IL-2 and behaved as a partial agonist. In murine T cell assays, the mutein was nearly inactive. Both cell lines tested expressed the high affinity form of the IL-2 receptor. On both cell types, Q126D displayed the ability to antagonize IL-2-mediated activity, although only partially in the human T cell assay.

Zhi-yong, W., et al., Acta Biochimica et Biophysica Sinica 25(5):558–560 (September 1993) performed substitution experiments on IL-2 at positions 62, 69, 99 and 126, demonstrating a 20-fold and 30-fold reduction in activity as compared to wt IL-2, with 62-Leu-IL-2 and 126-Asp-IL-2, respectively, in a mouse T-cell assay (CTLL-2). However, there is no teaching or suggestion that substitutions at position 126 may confer T-cell selective activity over NK cells, or indicate whether such changes would have a similar effect on human T cells.

Collins, L., et al., PNAS USA 85:7709–7713 (1988) reported that substition of Asp at position 20 with either Asn (D20N) or Lys (D20K) resulted in a loss of binding ~100- to 1,000-fold relative to human IL-2 for both the high (IL-2Rαβγ, termed p55/p70 in Collins, et al) and the intermediate affinity receptor (IL-2Rβγ, termed "p70" in Collins, et al). Binding to IL-2Rα appeared unaffected for both mutant proteins. This work teaches that disruption of binding to the intermediate affinity IL-2 receptor (IL-2Rβγ) will also lead to disruption of binding to the high affinity IL-2 receptor (IL-2Rαβγ), suggesting that differential binding or activation between IL-2Rβγ or IL-2Rαβγ is not achievable by substitution of Asp at position 20.

Berndt, W. G., et al., Biochemistry 33(21):6571–6577 (1994) used combinatorial cassette mutagenesis to simultaneously mutate positions 17–21 in native IL-2, which are suspected to interact with the intermediate affinity IL-2 receptor. Out of 2610 screened clones, only 42 were active. They found that positions 20 and 21 were of primary importance for biological activity. There is no suggestion or teaching of individual substitutions except for L21V.

U.S. Pat. No. 5,229,109 (Grimm, et al.) allegedly disclose low toxicity IL-2 analogs for use in immunotherapy and cancer treatment. The properties of two IL-2 analogs with substitutions at positions Arg38 (to Alanine) and Phe42 (to Lysine) were analyzed and compared to those of native IL-2. The analogs were found to be able to maintain their ability to bind to the intermediate IL-2 receptor, while binding only minimally to the so-called "high affinity" receptor. At this time the intermediate affinity receptor was thought to consist only of p75 (IL-2Rβ), and the high affinity receptor was thought to consist only of p55+p75 receptor complex (IL-2Rαβ). The analogs also maintained their ability to stimulate peripheral blood mononuclear cells to generate lymphokine activated killing (LAK). Notably, IL-1β and TNFα secretion were significantly reduced in response to the analogues, as compared to the native IL-2 molecule. The amino acid residues described in this patent are those that would interact specifically with IL-2Rα (p55); elimination of interactions with IL-2Rα would result in reduced activity on high affinity IL-2 receptor bearing cells, and would not affect activity to intermediate affinity IL-2 receptor bearing cells. Thus, generation of LAK cells (which are thought to be derived from NK cells) should be maintained. The muteins described herein are directed to amino acid residue positions 20, 88, and 126; these positions are thought to interact specifically with IL-2Rβ (p75; positions 20 and 88), and IL-2Rγ (not known at the time of the filing of the Grimm, et al patent; positions 126). As a consequence, interactions with IL-2Rα remain unchanged. Mechanistically, the muteins described by Grimm, et al, will have decreased interactions with the IL-2 high affinity receptor, but should have no effect on the IL-2 intermediate affinity receptor; the muteins described herein have the opposite characteristic, possessing a pronounced defect in their ability to interact with the IL-2 intermediate affinity receptor IL-2Rβγ, and show little or no defect in functional interactions with the IL-2 high affinity receptor, IL-2Rαβγ.

U.S. Pat. No. 5,206,344, (Goodson et al.) discloses muteins of IL-2 in which one of the amino acids of the mature native sequence of IL-2 is replaced by a cysteine residue, which are then prepared and conjugated through the replaced cysteine residue to a polymer selected from polyethylene glycol homopolymers or polyoxyethylated polyols, wherein the homopolymers are unsubstituted or substituted at one end with an alkyl group. These muteins are made via host expression of mutant genes encoding the muteins that have been changed from the genes for the parent proteins by site-directed mutagenesis. In addition, other species of IL-2 may be conjugated via the cysteine residue at position 125 of the mature IL-2 protein that is not necessary for the biological activity of the IL-2. There is no disclosure of mutations that confer reduced toxicity.

U.S. Pat. No. 4,959,314 (Lin et al.) discloses muteins of biologically active proteins such as IFN-β and IL-2 in which cysteine residues that are not essential to biological activity have been deleted or replaced with other amino acids to eliminate sites for intermolecular crosslinking or incorrect intramolecular disulfide bridge formation. These muteins are made via bacterial expression of mutant genes that encode the muteins that have been synthesized from the genes for the parent proteins by oligonucleotide-directed mutagenesis. There is no disclosure of mutations that confer reduced toxicity.

U.S. Pat. No. 5,116,943 (Halenbeck et al.) discloses that a biologically active reference therapeutic protein is protected against oxidation by a method involving substituting a conservative amino acid for each methionyl residue susceptible to chloramine T or peroxide oxidation, wherein additional, nonsusceptible methionyl residues are not so substituted. The oxidation-resistant mutein so produced is preferably a human mutein of interleukin-2 or interferon-β, and the conservative amino acid is most preferably alanine. There is no disclosure of mutations that confer reduced toxicity.

U.S. Pat. No. 4,853,332 (Mark et al.) is directed to IFN-γ and IL-2 muteins in which cysteine residues that are not essential to biological activity have been deleted or replaced with other amino acids to eliminate sites for intermolecular cross-linking or incorrect intramolecular disulfide bridge formation. The patent discloses that a substitution in IL-2 at cysteine 125 to serine results in a mutein with activity comparable to native IL-2.

U.S. Pat. No. 5,696,234 (Zurawski et al.) is directed to muteins of mammalian cytokines, and methods for screening for agonists and antagonists of mammalian cytokines. In particular, human IL-2 double mutein P82A/Q126D is demonstrated as having antagonist activity on murine Baf3 cells cotransfected with human α and β IL-2R subunits. Little agonist activity is shown. Also, murine IL-2 muteins are shown to exhibit partial agonist and antagonist activity on HT2 cells, in particular Q141D, Q141K, Q141V, and Q141L. No mutein activities are described that show or suggest a selective agonist effect for mutations at positions 20, 88 and 126.

Zurawski, et al, describe murine IL-2 muteins that have properties of being active on cells expressing IL-2Rαβγ but inactive on cells expressing IL-2Rβγ (Zurawski, G., *Trends Biotechnol.* 9: 250–257 (1991); Zurawski, S. M. and Zurawski, G. *Embo. J.* 11:3905–3910 (1992)). The murine IL-2 muteins that exhibited these properties had the substitutions Asp-34 to Ser or Thr, and Gln-141 to Lys. Asp-34 and Gln-141 of mouse IL-2 appear equivalent to Asp-20 and Gln-141 of human IL-2, respectively. Although these references refer to "selective agonist" IL-2 muteins, they do not describe their potential as being less toxic, but rather as being potential antagonists of endogenous IL-2.

EP 0267 795 A2 (Zurawski et al.) discloses a variety of mouse IL-2 muteins throughout the sequence, including some containing deletions and/or substitutions within the first thirty N-terminal amino acid residues which are biologically competent, but it does not include, discuss or suggest the amino acid substitutions disclosed here at the equivalent mouse IL-2 residues. There exists a need for an improved IL-2 molecule which has reduced toxicity and is more generally tolerated.

Taniguchi et al., U.S. Pat. No. 4,738,927 is directed to a recombinant DNA which comprises a recombinant DNA encoding a polypeptide which possesses a biological activity of IL-2, wherein said activity is promotion of growth of a cytotoxic T-lymphocyte cell line, and a vector DNA capable of propagating in a prokaryotic or eukaryotic cell, the coding sequence of said gene being located at a position downstream of a promoter sequence, wherein said polypeptide has 132 to 134 amino acids in total in the amino acid sequence of the polypeptide. It also describes a gene, recombinant DNA vectors, host cells, and methods of recombinantly producing native IL-2. Taniguchi et al. do not describe any variants or muteins, and do not teach which positions in the protein are responsible for signaling or binding activity.

It is clear that IL-2 muteins that do not exhibit the dose-limiting toxicity of the prior art recombinant IL-2 muteins are needed to take therapeutic advantage of the potential of this cytokine.

SUMMARY OF THE INVENTION

The invention is directed to a polypeptide comprising a human IL-2 mutein numbered in accordance with wild-type IL-2 wherein said human IL-2 is substituted at at least one of positions 20, 88 or 126, whereby said mutein preferentially activates T cells over NK cells. This invention realizes a less toxic IL-2 mutein that allows greater therapeutic use of this interleukin.

Further, the invention is directed to IL-2 muteins having single mutations at positions Aspartate 20, Asparagine 88, and Glutamine 126. Specific muteins are represented by the designators D20X, N88X, and Q126X, where "X" is a specific amino. acid that when substituted in human IL-2, confers selective activity for cells expressing the IL-2Rαβγ receptor (e.g. T cells) in preference to cells expressing the IL-2Rβγ receptor (e.g., NK cells). Muteins exhibiting greater than 1000-fold selectivity include D20H, D20I, N88G, N88I, N88R, and Q126L. In particular, these muteins also exhibit essentially wild-type IL-2 activity on T cells. Other mutations are also identified that provide selectivity of less than 1000-fold but greater than 10-fold. The invention also includes polynucleotides coding for the muteins of the invention, vectors containing the polynucleotides, transformed host cells, pharmaceutical compositions comprising the muteins, and therapeutic methods of treatment using the muteins.

The invention is also directed to a method of selecting IL-2 muteins through evaluation in assays utilizing IL-2Rαβγ in comparison with IL-2Rβγ, wherein the activity of an IL-2 mutein is increased relative to wt IL-2 in one assay preferentially to the other. IL-2Rαβγ and IL-2Rβγ are the individual receptor subunit ectodomains in appropriate combination, and are used to measure directly the binding of IL-2 muteins to each receptor complex. The IL-2αβγ assay utilizes a response from an IL-2αβγ-bearing cell type, and the IL-2βγ assay utilizes a response from an IL-2βγ-bearing cell type. The IL-2αβγ-bearing cell is a PHA-blast, and the IL-2βγ-bearing cell is a NK cell. The assay is proliferation for both the IL-2αβγ-bearing cell type and the IL-2βγ-bearing cell type.

The invention is also directed to a vector comprising the polynucleotide encoding a mutein of this invention, the vector directing the expression of a human IL-2 mutein having PHA-blast cell activating activity but having reduced NK cell activating activity, the vector being capable of enabling transfection of a target organism and subsequent in vivo expression of said human IL-2 mutein coded for by said polynucleotide.

The invention is also directed to a method of treating a patient afflicted with an IL-2 treatable condition by administering a therapeutically effective amount of a human IL-2 mutein numbered in accordance with wild-type IL-2 having PHA-blast activating activity but having reduced NK cell activating activity. This method is applicable wherein the IL-2 treatable condition is HIV, Cancer, autoimmune disease, infectious disease, vaccine adjuvant in Cancer vaccine and conventional vaccine therapy, for immune stimulation in the elderly or otherwise immunocompromised, as well as in human SCID patients, or other therapeutic application requiring stimulation of the immune system.

BRIEF DESCRIPTION OF THE DRAWINGS

FIGS. 1 to 7 show the dose-response curves of wt human IL-2 (IL-2) and D20H (FIG. 1), IL-2 and D20I (FIG. 2), IL-2 and N88G (FIG. 3), IL-2 and N88I (FIG. 4), IL-2 and N88R (FIG. 5), IL-2 and Q126E, (FIG. 6), and IL-2 and Q126L (FIG. 7). A: Individual dose response of IL-2 (closed circles) and mutein (open circles) in the primary human T cell proliferation assay (PHA-blasts). B: Individual dose response of IL-2 (closed triangles) and mutein (open triangles) in the primary human NK cell proliferation assay.

FIGS. 8A–8D. Toxicity of PROLEUKIN™ in chimpanzee was evaluated in two animals (X-159, triangles, and X-124, squares), as compared to vehicle control (X-126, diamonds). Toxicity was evaluated- by renal parameters (Blood Urea Nitrogen (BUN), A; Creatinine, B) and hepatic function (Total bilirubin, C; ALT, D).

FIG. 9. Graph of body weight percent change over 30 days. Body weight for animals treated with IL-2/N88R (triangles), PROLEUKIN (squares) or vehicle (diamonds) was measured on the days indicated.

FIGS. 10A–10D. Lymphocytes (A), total white cells (B), neutrophils (C), and platelets (D) for animals treated with IL-2/N88R (triangles), PROLEUKIN (squares) or vehicle (diamonds) were evaluated on days indicated.

FIGS. 11A–11D. Blood urea nitrogen (A, BUN), creatinine (B), phosphorus (C), and anion gap (D) for animals treated with IL-2/N88R (triangles), PROLEUKIN (squares) or vehicle (diamonds) were evaluated on days indicated.

FIGS. 12A–12D. Total bilirubin (A), ALT (B), Fibrinogen (C), and activated prothrombin time (D) for animals treated with IL-2/N88R (triangles), PROLEUKIN (squares) or vehicle (diamonds) were evaluated on days indicated.

FIGS. 13A–13D. Blood levels of sodium (A), chloride ion (B), calcium (C), and potassium (D) for animals treated with IL-2/N88R.(triangles), PROLEUKIN (squares) or vehicle (diamonds) were evaluated on days indicated.

FIGS. 14A–14C. Albumin levels in blood (A), hematocrit (B), and hemoglobin (C) for animals treated with IL-2/N88R (triangles), PROLEUKIN (squares) or vehicle (diamonds) were evaluated on days indicated.

FIGS. 15A–15C. The effect of IL-2/N88R (squares), PROLEUKIN (diamonds), and vehicle (triangles) are indicated for the total T cell population (A, CD3+ cells), CD4+ T cell population (B), and the CD8+ T cell population (C).

FIGS. 16A–16C. The effect of IL-2/N88R (squares), PROLEUKIN (diamonds), and vehicle (triangles) are indicated for the total T cell population (A, CD3+cells), CD4+T cell population (B), and the CD8+ T cell population (C).

FIG. 17. Effect of IL-2IN88R and PROLEUKIN on T cell activation with respect to the mean of fluorescence of CD25 positive cells. The effect of IL-2/N88R (squares), PROLEUKIN (diamonds), and vehicle (triangles) are indicated for the CD3+CD4+ T cell population. Insufficient numbers of CD3+/CD8+ cells were obtained to evaluate mean of fluorescence on this population.

FIGS. 18A–18D. The effect of IL-2IN88R (squares), PROLEUKIN (diamonds), and vehicle (triangles) are indicated for the CD4+ T cell population (A, CD3+/CD4+ cells), the CD8+ T cell population (B, CD3+/CD8+ cells), total T cell population (C, CD3+ cells), and the NK cell population (D, CD3−/CD16+ cells).

FIG. 19. Graph of lung metastases versus dose in mice treated with PROLEUKIN (open circles) or IL-2/N88R (closed circles). Lung metastasis were counted at the conclusion of the study.

FIG. 20. Plasmid map of the IL2N88R vector pBC1IL2SA.

DESCRIPTION OF THE PREFERRED EMBODIMENTS

A. Background

The action of IL-2 on T cells is mediated by binding to IL-2 receptor proteins. Distinct cell surface proteins on T cells bind IL-2. The first to be identified is a single polypeptide, called IL-2Rα, which is a 55 kD polypeptide (p55) that appears upon T cell activation and was originally called Tac (for T activation) antigen. IL-2Rα binds IL-2 with a $K_d$ of approximately $10^{-8}$ M, and is also known as the "low affinity" IL-2 receptor. Binding of IL-2 to cells expressing only IL-2Rα does not lead to any detectable biologic response.

The second IL-2 receptor is a binding complex composed of IL-2Rb and IL-2Rg; IL-2Rg, a 64 kD polypeptide, is also known as the common γ ($\gamma_c$) chain because it is shared among a number of cytokine receptors. IL-2Rb is about 70 to 75 kD (called variously p70 or p75) and is a member of the type I cytokine receptor family characterized by the two cysteine/WSXWS motif. IL-2Rβ is expressed coordinately with $\gamma_c$. The affinity of binding of IL-2 to IL-2Rβ$\gamma_c$ is higher than that to IL-2Rα, with a $K_d$ of approximately $10^{-9}$ M; it is also known as the "intermediate affinity" IL-2 receptor. IL-2 causes growth of cells expressing IL-2Rβ$\gamma_c$, with half maximal growth stimulation occurring at the same concentration of IL-2 that produces half maximal binding (i.e., $1 \times 10^{-9}$ M). IL-2Rβ$\gamma_c$ is the same signaling receptor complex that can bind to IL-15.

The third known IL-2 receptor complex is the IL-2Rαβ$\gamma_c$ complex. Cells that express both IL-2Rα and IL-2Rβ$\gamma_c$ can bind IL-2 much more tightly, with a $K_d$ of approximately $10^{-11}$ M, and so it is also known as the "high affinity" complex. Growth stimulation of such cells occurs at a similarly low IL-2 concentration. Both IL-2 binding and growth stimulation can be blocked by antibodies to IL-2Rα, IL-2Rβ, or $\gamma_c$ and most efficiently by a combination of antibodies to multiple receptor subunits. These observations suggest that IL-2Rα forms a complex with IL-2Rβ$\gamma_c$, increasing the affinity of the signaling receptor for IL-2 and thereby allowing a growth signal to be delivered at significantly lower IL-2 concentrations. It is believed that IL-2 first binds rapidly to IL-2Rα, and this facilitates association with IL-2Rβ$\gamma_c$. Resting T cells express IL-2Rβ$\gamma_c$ but only low amounts of IL-2Rα; increasing the surface expressed IL-2Rα can be stimulated by IL-2. Upon antigen receptor-mediated T cell activation, IL-2Rα is rapidly expressed, thereby reducing the concentration of IL-2 needed for growth stimulation. Binding of IL-2 to the IL-2Rαβ$\gamma_c$ complex results in signal transduction through a Jak/STAT signaling pathway.

We have discovered muteins of human IL-2 that preferentially activate T cells (PHA-blasts; cells which express the high affinity IL-2 receptor IL-2Rαβγ) in relation to Natural Killer (NK) cells (cells which express the intermediate affinity IL-2 receptor IL-2Rβγ). Muteins that substitute Asp-20 with Histidine (D20H) or Isoleucine (D20I), Asn-88 with Arginine (N88R), Glycine (N88G), or Isoleucine (N88I), or Gln-126 with Leucine (Q126L), or Glutamate (Q126E) exhibit unexpectedly full IL-2 activity on PHA-blasts, and little (if any) activity on NK cells. Previous studies of human IL-2 muteins have relied on murine cellular systems of analysis, and when human cells have been used, have not utilized cells expressing only IL-2Rβγ (such as NK cells). Additionally, those studies utilizing human PHA-blasts have shown that the substitution of Asp-20 (with Leu, Arg, Asp, or Lys; Xu, et. al., *Eur. Cytokine Netw*, 6, 237–244 (1995)) or Gln-126 (with Asp; Buchli and Ciardelli, *Arch. Biochem. Biophys*, 307(2): 411–415, (1993)) result in human IL-2 muteins having severely compromised activity. Previous studies using murine IL-2 identified mouse IL-2 muteins with differing activities (Zurawski, et.al., *EMBO J*, 12 5113–5119 (1993)), but none of the mutations that yielded these results were suggestive of those identified in the work described herein. Human IL-2 muteins containing identical mutations at synonymous positions with murine IL-2 muteins do not exhibit similar activities, and therefor suggest that the murine examples are not predictive of human functionality. No studies of human IL-2 muteins are known to the inventors comparing relative activities on human cells expressing the IL-2 receptor IL-2Rαβγ (e.g., PHA-blasts) in relation to expressing the IL-2 receptor IL-2Rβγ (e.g., NK cells). It is expected that analysis in vivo will confirm that the muteins described will have an improved therapeutic index over wild-type human IL-2 through the reduction of toxicity, thus providing therapeutically useful compounds for the treatment of disorders requiring immune system stimulation.

Interleukin 2 (IL-2) is currently in use in the clinic for the treatment of metastatic renal cancer. However, its severe toxicity has limited its use to only a subset of the healthiest of patients, and dose-limiting toxicity is presumed to compromise its overall efficacy. Acute toxicity of IL-2 has been proposed to be mediated through activation of NK cells, whereas the efficacy is mediated by the direct activation of T cells (Jacobson, et.al., *Proc Natl Acad Sci USA* (United States), Sep. 17, 1996, 93(19) p10405–10; Smith K A, *Blood* 1993, 81(6) p1414–23; Kaplan, et.al., *Biotechnology*, 10(2) p157–62). T cells express a different receptor for IL-2 than do NK cells (T cells: IL-2Rαβγ, the high affinity IL-2 receptor; NK cells: IL-2Rβγ, the intermediate affinity IL-2 receptor). The human IL-2 muteins described herein selectively activate the T cell IL-2 receptor and not the NK cell IL-2 receptor.

Low-dose therapy with IL-2 has been utilized to circumvent directly activating NK cells with some success (Jacobson, et. al. (1996). *Proc Natl Acad Sci USA* 93: 10405–10). This strategy incorporated the concept that at low-doses of IL-2, only the high affinity IL-2 receptor will be activated to the exclusion of the intermediate affinity IL-2 receptor. The intermediate affinity form of the IL-2 receptor, IL-2Rβγ, is expressed on NK cells, while T cells express the high affinity form, IL-2Rαβγ.

However, the inventors approached the toxicity problem from a different angle. Disruption of the interactions of IL-2 with IL-2Rβ and/or IL-2Rγ through appropriate modification of specific binding residues on the binding surface of IL-2 were hypothesized to prevent effective binding (and thus activation) to cells expressing only IL-2Rβγ. However, on cells expressing IL-2Rαβγ, initial binding to IL-2Rα, and thus binding to the cell, will still occur, and so the low-dose therapy suggested by Jacobs et al. may still manifest toxic side effects. By virtue of binding to IL-2Rα, effective recruitment of IL-2Rβ and IL-2Rγ can occur on the cell surface despite the impaired interactions of the modified IL-2 with IL-2Rβ and/or IL-2Rγ. A signaling-competent IL-2/IL-2Rαβγ complex can thus be formed. An IL-2 variant able to selectively activate the high affinity IL-2 receptors on T cells in preference to the intermediate affinity IL-2 receptors on NK cells we believe may have an increased therapeutic index over wild-type IL-2 due to a reduced toxicity profile. An IL-2 variant with an increased therapeutic index would have a significantly expanded range of use in both the treatment of cancer (as a direct and/or adjunct therapy) and immunodeficiency (e.g., HIV and tuberculosis). Other potential uses of IL-2 are derived from its immunostimulatory activity, and include besides direct treatment of cancer, immunodeficiency, such as HIV or human SCID patients; infectious disease, such as tuberculosis; as an adjuvant in "cancer vaccine" strategies; and for immune system stimulation indications, such as enhancing standard vaccination protocols or for the treatment of the elderly.

Appropriate substitution at Asp-20, Asn-88, or Gln-126 reduced the binding interactions for either IL-2Rβ (Asp-20 and Asn-88) or IL-2Rγ (Gln-126). The net effect of such substitutions resulted in IL-2 muteins that retained activity on human T cells, and have reduced activity on human NK cells.

As it was not possible to predict the outcome of a given substitution prior to evaluation in the T and NK cell assays, all possible natural amino acid substitutions (except Cys) were made at positions Asp-20, Asn-88 and Gln-126, and a limited but diverse set of mutations were made at position Asp-84 to test whether they indeed interacted with IL-2Rβ. Additional mutations would be tested at position Asp-84 if effects on apparent IL-2Rβ interactions were observed. Data for forty-six separate substitutions at those positions is presented in Table 1, infra.

Mutations were introduced using site-directed mutagenesis on wild-type human IL-2 cDNA. Correct clones were subcloned to an expression vector suitable for expression in a heterologous system (e.g., *E. coli*, baculovirus, yeast or mammalian cells such as, for example, Chinese Hamster Ovary (CHO) cells). Purified proteins were tested in T cell (PHA-blast) proliferation and NK proliferation assays. Different responses generated by individual muteins between these assays, i.e., $EC_{50}$, indicate mutations that effect these activities. Specifically, muteins that stimulate a relatively stronger response in the PHA-blast (T cell) assay (vs. wild-type IL-2) as compared to the response on NK cell assay (vs. wild-type IL-2) will suggest substitutions that provide cellular specificity based on the ability of specific muteins to bind to and activate IL-2Rαβγ expressed on these cells, but unable to bind, and thus not activate, cells expressing only IL-2Rβγ. IL-2 muteins exhibiting this property will thus possess in vivo the immunostimulatory properties of IL-2 with reduced IL-2 therapy-associated toxicities of vascular leak and hypotension.

B. Definitions

Deposit of a CHO cell line used to produce the recombinant protein described herein was made at the American Type Culture Collection (ATCC), P.O. Box 1549, Manassas, Va. 20108, USA, on May 5, 1999, Deposit No. PTA-8. Since the strain referred to is being maintained under the terms of the Budapest Treaty, it will be made available to a patent office signatory to the Budapest Treaty.

As used herein, “wild type IL-2” means IL-2, whether native or recombinant, having the 133 normally occurring amino acid sequence of native human IL-2 (less the signal peptide, consisting of an additional 20 N-terminal amino acids), whose amino acid sequence is described in Fujita, et. al., *PNAS USA*, 80, 7437–7441 (1983), with or without an additional N-terminal Methionine which is necessarily included when the protein is expressed as an intracellular fraction in *E. coli.*

As used herein, “IL-2 mutein” means a polypeptide wherein specific substitutions to the human mature interleukin-2 protein have been made. Table 1, infra, discloses forty-six individual substitution IL-2 muteins made, and their corresponding relative activity data. Preferred embodiments include those muteins having at least 100-fold relative activity. Particularly preferred embodiments include the following, which exhibit greater than 1000-fold relative activity: aspartate (Asp) residue (D) at position 20 (“D20”), when numbered in accordance with wild type IL-2, is substituted with isoleucine, (“D20I”) or Histidine (“D20H”); the asparagine residue (Asn) at position 88 (N88) has been substituted with Isoleucine (N88I), Glycine (N88G), or Arginine (N88R); and the glutamine residue (Gln) at position 126 (Q126) has been substituted with Leucine (Q126L) or Glutamate (Q126E) or Aspartate (Q126D). The preferred IL-2 muteins have an amino acid sequence identical to wild type IL-2 at the other, non-substituted residues. However, the IL-2 muteins of this invention may also be characterized by amino acid insertions, deletions, substitutions and modifications at one or more sites in or at the other residues of the native IL-2 polypeptide chain. In accordance with this invention any such insertions, deletions, substitutions and modifications may result in an IL-2 mutein that retains a PHA-blast selective activity while having reduced ability to activate NK cells, and come within the scope of this patent.

Combining the preferred or particularly preferred substitutions described above in a single recombinant IL-2 molecule may result in combination mutants having activity similar to that disclosed herein by the single mutants. For example, it may be expected that an IL-2 molecule having a combination of two or more mutations selected from Table 1 may result in a T cell selective IL-2 agonist with relative activity similar to the relative -activity of the single substitutions disclosed herein. Combination mutants come within the spirit and scope of the present invention.

We prefer conservative modifications and substitutions at other positions of IL-2 (i.e., those that have a minimal effect on the secondary or tertiary structure of the mutein). Such conservative substitutions include those described by Dayhoff in *The Atlas of Protein Sequence and Structure* 5 (1978), and by Argos in EMBO J., 8:779–785 (1989). For example, amino acids belonging to one of the following groups represent conservative changes:

ala, pro, gly, gln, asn, ser, thr;
cys, ser, tyr, thr;
val, ile, leu, met, ala, phe;
lys, arg, his;
phe, tyr, trp, his; and
asp, glu.

We also prefer modifications or substitutions that do not introduce sites for additional intermolecular crosslinking or incorrect disulfide bond formation. For example, IL-2 is known to have three cys residues, at wild-type positions 58, 105 and 125 of the mature sequence.

By “numbered in accordance with wild type IL-2” we mean identifying a chosen amino acid with reference to the position at which that amino acid normally occurs in the mature sequence of wild type IL-2. Where insertions or deletions are made to the IL-2 mutein, one of skill in the art will appreciate that the Asp normally occurring at position 20 may be shifted in position in the mutein. However, the location of the shifted Asp can be readily determined by inspection and correlation of the flanking amino acids with those flanking Asp in wild type IL-2.

The term “cell types having the IL-2Rαβγ receptor” means the cells known to have this receptor type, i.e., T cells, activated T cells, B cells, activated monocytes, and activated NK cells. The term “cell types having the IL-2Rβγ receptor” means the cells known to have that receptor type, i.e., B cells, resting monocytes, and resting NK cells.

The IL-2 muteins of the present invention can be produced by any suitable method known in the art. Such methods include constructing a DNA sequence encoding the IL-2 muteins of this invention and expressing those sequences in a suitably transformed host. This method will produce the recombinant muteins of this invention. However, the muteins of this invention may also be produced, albeit less preferably, by chemical synthesis or a combination of chemical synthesis and recombinant DNA technology. Batch-wise production or perfusion production methods are generally within the skill of the art. See Freshey, R. I. (ed), “Animal Cell Culture: A Practical Approach,” 2nd ed., 1992, IRL Press, Oxford, England; Mather, J. P. “Laboratory Scaleup of Cell Cultures (0.5–50 liters),” *Methods Cell Biology* 57: 219–527 (1998); Hu, W. S., and Aunins, J. G., “Large-scale Mammalian Cell Culture,” *Curr Opin Biotechnol* 8: 148–153 (1997); Konstantinov, K. B., Tsai, Y., Moles, D., Matanguihan, R., “Control of long-term perfusion Chinese hamster ovary cell culture by glucose auxostat.," *Biotechnol Prog* 12:100–109 (1996).

In one embodiment of a recombinant method for producing a mutein of this invention, a DNA sequence is constructed by isolating or synthesizing a DNA sequence encoding the wild type IL-2 and then changing the codon for Asp20 to a codon for Isoleucine (I) by site-specific mutagenesis. This technique is well known. See, e.g., Mark et al., "Site-specific Mutagenesis Of The Human Fibroblast Interferon Gene", *Proc. Natl. Acad. Sci. USA* 81, pp. 5662–66 (1984); and U.S. Pat. No. 4,588,585, incorporated herein by reference.

Another method of constructing a DNA sequence encoding the IL-2 muteins of this invention would be chemical synthesis. This for example includes direct synthesis of a peptide by chemical means of the protein sequence encoding for an IL-2 mutein exhibiting the properties described in the invention. This method may incorporate both natural and unnatural amino acids at positions that affect the interactions of IL-2 with the IL-2Rβ or IL-2Rγ. Alternatively a gene which encodes the desired IL-2 mutein may be synthesized by chemical means using an oligonucleotide synthesizer. Such oligonucleotides are designed based on the amino acid sequence of the desired IL-2 mutein, and preferably selecting those codons that are favored in the host cell in which the recombinant mutein will be produced. In this regard, it is well recognized that the genetic code is degenerate—that an amino acid may be coded for by more than one codon. For example, Phe (F) is coded for by two codons, TTC or TTT, Tyr (Y) is coded for by TAC or TAT and his (H) is coded for by CAC or CAT. Trp (W) is coded for by a single codon, TGG. Accordingly, it will be appreciated that for a given DNA sequence encoding a particular IL-2 mutein, there will be many DNA degenerate sequences that will code for that IL-2 mutein. For example, it will be appreciated that in addition to the preferred DNA sequence for mutein D20I shown in SEQ ID NO:1, there will be many degenerate DNA sequences that code for the IL-2 mutein shown. These degenerate DNA sequences are considered within the scope of this invention. Therefore, "degenerate variants thereof" in the context of this invention means all DNA sequences that code for and thereby enable expression of a particular mutein.

The DNA sequence encoding the IL-2 mutein of this invention, whether prepared by site directed mutagenesis, chemical synthesis or other methods, may or may not also include DNA sequences that encode a signal sequence. Such signal sequence, if present, should be one recognized by the cell chosen for expression of the IL-2 mutein. It may be prokaryotic, eukaryotic or a combination of the two. It may also be the signal sequence of native IL-2. The inclusion of a signal sequence depends on whether it is desired to secrete the IL-2 mutein from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild-type IL-2 signal sequence be used.

Standard methods may be applied to synthesize a gene encoding an IL-2 mutein according to this invention. For example, the complete amino acid sequence may be used to construct a back-translated gene. A DNA oligomer containing a nucleotide sequence coding for IL-2 mutein may be synthesized. For example, several small oligonucleotides coding for portions of the desired polypeptide may be synthesized and then ligated. The individual oligonucleotides typically contain 5' or 3' overhangs for complementary assembly.

Once assembled (by synthesis, site-directed mutagenesis or another method), the DNA sequences encoding an IL-2 mutein of this invention will be inserted into an expression vector and operatively linked to an expression control sequence appropriate for expression of the IL-2 mutein in the desired transformed host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of host. A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including col El, pCRl, pER32z, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2 µ plasmid and derivatives thereof. Useful vectors for insect cells include pVL 941. We prefer pFastBac™ 1 (GibcoBRL, Gaithersburg, Md.). Cate et al., "Isolation Of The Bovine And Human Genes For Mullerian Inhibiting Substance And Expression Of The Human Gene In Animal Cells", Cell, 45, pp. 685–98 (1986).

In addition, any of a wide variety of expression control sequences may be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example PL, the control regions of fd coat protein, the promoter for 3-phosphoglycerate kinase or other glycolytic enzymes, the promoters of acid phosphatase, e.g., PhoA, the promoters of the yeast α-mating system, the polyhedron promoter of Baculovirus, and other sequences known to control the expression of genes of prokaryotic or eukaryotic cells or their viruses, and various combinations thereof.

Any suitable host may be used to produce the IL-2 muteins of this invention, including bacteria, fungi (including yeasts), plant, insect, mammal, or other appropriate animal cells or cell lines, as well as transgenic animals or plants. More particularly, these hosts may include well known eukaryotic and prokaryotic hosts, such as strains of *E. coli, Pseudomonas, Bacillus, Streptomyces*, fungi, yeast, insect cells such as *Spodoptera frugiperda* (Sf9), animal cells such as Chinese hamster ovary (CHO) and mouse cells such as NS/O, African green monkey cells such as COS 1, COS 7, BSC 1, BSC 40, and BNT 10, and human cells, as well as plant cells in tissue culture. For animal cell expression, we prefer CHO cells and COS 7 cells in cultures and particularly the CHO cell line CHO (DHFR-) or the HKB line.

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, preferred vectors for use in this invention include those that allow the DNA encoding the IL-2 muteins to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrafolate Reductase cDNA Gene: Analysis Of Signals Utilized For Efficient Expression", Mol. Cell. Biol., 2, pp. 1304–19 (1982)) or glutamine synthetase ("GS") amplification (see, e.g., U.S. Pat. No. 5,122,464 and European published application 338,841).

In selecting an expression control sequence, a variety of factors should also be considered. These include, for example, the relative strength of the sequence, its controllability, and its compatibility with the actual DNA sequence encoding the IL-2 mutein of this invention, particularly as regards potential secondary structures. Hosts should be selected by consideration of their compatibility with the chosen vector, the toxicity of the product coded for by the DNA sequences of this invention, their secretion characteristics, their ability to fold the polypeptides correctly, their fermentation or culture requirements, and the ease of purification of the products coded for by the DNA sequences.

Within these parameters one of skill in the art may select various vector/expression control sequence/host combinations that will express the desired DNA sequences on fermentation or in large scale animal culture, for example, using CHO cells or COS 7 cells.

The IL-2 muteins obtained according to the present invention may be glycosylated or unglycosylated depending on the host organism used to produce the mutein. If bacteria are chosen as the host then the IL-2 mutein produced will be unglycosylated. Eukaryotic cells, on the other hand, will glycosylate the IL-2 muteins, although perhaps not in the same way as native-IL-2 is glycosylated. The IL-2 mutein produced by the transformed host can be purified according to any suitable method. Various methods are known for purifying IL-2. See, e.g Current Protocols in Protein Science, Vol 2. Eds: John E. Coligan, Ben M. Dunn, Hidde L. Ploehg, David W. Speicher, Paul T. Wingfield, Unit 6.5 (Copyright 1997, John Wiley and Sons, Inc. We prefer refolding from inclusion bodies generated in E. coli, or from conditioned medium from either mammalian or yeast cultures producing a given mutein using cation exchange, gel filtration, and or reverse phase liquid chromatography. See Examples 1 (E. coli) and 10 (CHO cell perfusion) below.

The biological activity of the IL-2 muteins of this invention can be assayed by any suitable method known in the art. Such assays include PHA-blast proliferation and NK cell proliferation. Muteins of appropriate activity, ie., fully active on IL-2Rαβγ, with reduced activity on cells bearing IL-2Rβγ, will be confirmed using the two assays. The "relative activity" of a mutein is measured with respect to wild-type IL-2, and as described further in the examples, is the ratio of the activity of PHA-blast proliferation to NK cell proliferation.

The IL-2 mutein of this invention will be administered at a dose approximately paralleling that or greater than employed in therapy with wild type native or recombinant IL-2. An effective amount of the IL-2 mutein is preferably administered. An "effective amount" means an amount capable of preventing or lessening the severity or spread of the condition or indication being treated. It will be apparent to those of skill in the art that the effective amount of IL-2 mutein will depend, inter alia, upon the disease, the dose, the administration schedule of the IL-2 mutein, whether the IL-2 mutein is administered alone or in conjunction with other therapeutic agents, the serum half-life of the composition, and the general health of the patient.

The IL-2 mutein is preferably administered in a composition including a pharmaceutically acceptable carrier. "Pharmaceutically acceptable carrier" means a carrier that does not cause any untoward effect in patients to whom it is administered. Such pharmaceutically acceptable carriers are well known in the art. We prefer 2% HSA/PBS at pH 7.0.

The IL-2 muteins of the present invention can be formulated into pharmaceutical compositions by well known methods. See, e.g., Remington's Pharmaceutical Science by E. W. Martin, hereby incorporated by reference, describes suitable formulations. The pharmaceutical composition of the IL-2 mutein may be formulated in a variety of forms, including liquid, gel, lyophilized, or any other suitable form. The preferred form will depend upon the particular indication being treated and will be apparent to one of skill in the art.

The IL-2 mutein pharmaceutical composition may be administered orally, by aerosol, intravenously, intramuscularly, intraperitoneally, intradermally or subcutaneously or in any other acceptable manner. The preferred mode of administration will depend upon the particular indication being treated and will be apparent to one of skill in the art. The pharmaceutical composition of the IL-2 mutein may be administered in conjunction with other therapeutic agents. These agents may be incorporated as part of the same pharmaceutical composition or may be administered separately from the IL-2 mutein, either concurrently or in accordance with any other acceptable treatment schedule. In addition, the IL-2 mutein pharmaceutical composition may be used as an adjunct to other therapies.

Accordingly, this invention provides compositions and methods for the treatment of HIV, Cancer, autoimmune disease, infectious disease, vaccine adjuvant in Cancer vaccine and conventional vaccine therapy, for immune stimulation in the elderly or otherwise immunocompromised individuals, as well as in human SCID patients, or other therapeutic application requiring general stimulation of the immune system in any suitable animal, preferably a mammal, most preferably human. As previously noted in the Background section, IL-2 has many effects. Some of these are stimulation of PHA-blasts, resting T cells, B cells, monocytes, and NK cells., etc.; muteins described herein will have activities on cell types expressing only the high affinity IL-2 receptor, such as resting T cells, but not the intermediate affinity IL-2 receptor, such as NK cells or monocytes.

Also contemplated is use of the DNA sequences encoding the IL-2 muteins of this invention in gene therapy applications. Gene therapy applications contemplated include treatment of those diseases in which IL-2 is expected to provide an effective therapy due to its T cell activity, e.g., HIV, Cancer, autoimmune disease, infectious disease, vaccine adjuvant in Cancer vaccine and conventional vaccine therapy, for immunestimulation in the elderly or otherwise immunocompromised, as well as in human SCID patients, and diseases that are otherwise responsive to IL-2 or infectious agents sensitive to IL-2-mediated immune response.

Local delivery of IL-2 muteins using gene therapy may provide the therapeutic agent to the target area. Both in vitro and in vivo gene therapy methodologies are contemplated. Several methods for transferring potentially therapeutic genes to defined cell populations are known. See, e.g., Mulligan, "The Basic Science Of Gene Therapy", *Science*, 260: 926–31 (1993). These methods include:

1) Direct gene transfer. See, e.g., Wolff et al., "Direct Gene transfer Into Mouse Muscle In Vivo", *Science*, 247: 1465–68 (1990);

2) Liposome-mediated DNA transfer. See, e.g., Caplen at al., "Liposome-mediated CFTR Gene Transfer To The Nasal Epithelium Of Patients With Cystic Fibrosis", *Nature Med.* 3: 39–46 (1995); Crystal, "The Gene As A Drug", *Nature Med.* 1:15–17 (1995); Gao and Huang, "A Novel Cationic Liposome Reagent For Efficient Transfection Of Mammalian Cells", *Biochem. Biophys. Res. Comm.*, 179:280–85 (1991);

3) Retrovirus-mediated DNA transfer. See, e.g., Kay et al., "In Vivo Gene Therapy Of Hemophilia B: Sustained Partial Correction In Factor IX-Deficient Dogs", *Science*, 262:117–19 (1993); Anderson, "Human Gene Therapy", *Science*, 256:808–13 (1992).

4) DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., "The Use Of DNA Viruses As Vectors For Gene Therapy", *Gene Therapy*, 1:367–84 (1994); U.S. Pat. No. 4,797,368, incorporated herein by reference, and U.S. Pat. No. 5,139,941, incorporated herein by reference.

The choice of a particular vector system for transferring the gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity.

Adenoviruses have the advantage that they have a broad host range, can infect quiescent or terminally differentiated cells, such as neurons or hepatocytes, and appear essentially non-oncogenic. See, e.g., Ali et al., supra, p. 367. Adenoviruses do not appear to integrate into the host genome. Because they exist extrachromosomally, the risk of insertional mutagenesis is greatly reduced. Ali et al., supra, p. 373.

Adeno-associated viruses exhibit similar advantages as adenoviral-based vectors. However, AAVs exhibit site-specific integration on human chromosome 19. Ali et al., supra, p. 377.

In a preferred embodiment, the IL-2 mutein-encoding DNA of this invention is used in gene therapy for immunodeficiency diseases such as HIV; infectious diseases such as tuberculosis; and cancers, such as renal carcinoma.

According to this embodiment, gene therapy with DNA encoding the IL-2 muteins of this invention is provided to a patient in need thereof, concurrent with, or immediately after diagnosis.

This approach takes advantage of the selective activity of the IL-2 muteins of tis invention to prevent undesired toxicity and adverse events. The skilled artisan will appreciate that any suitable gene therapy vector containing IL-2 mutein DNA may be used in accordance with this embodiment. The techniques for constructing such a vector are known. See, e.g., Anderson, W. F., Human Gene Therapy, *Nature*, 392 25–30 (1998); Verma, I. M., and Somia, N., Gene Therapy—Promises, Problems, and Prospects, *Nature*, 389 239–242 (1998). Introduction of the IL-2 mutein DNA-containing vector to the target site may be accomplished using known techniques.

In order that this invention may be better understood, the following examples are set forth. These examples are for the purpose of illustration only, and are not to be construed as limiting the scope of the invention in any manner. All publications mentioned herein are incorporated by reference in their entirety.

C. EXAMPLES

Example 1

Production of Muteins in *E. coli*.

Muteins were generated by site-directed mutagenesis using primers containing codons corresponding to the desired mutation essentially as described by Kunkel T A, Roberts J D, and Zakour R A, "Rapid and efficient site-specific mutagenesis without phenotypic selection" (1987), *Methods Enzymol* 154: 367–382. Briefly, human IL-2 cDNA containing the restriction enzyme sites Bam HI and Xba I was subcloned into the M13 phage vector M13 mpl9 (New England Biolabs, Beverly, Mass.) using the same sites. Wild-type IL-2 cDNA was obtained using Polymerase Chain Reaction ("PCR") from a cDNA pool generated from mRNA isolated from human peripheral blood lymphocytes induced 24 hours with phorbol 12-myristate 13-acetate (10 ng/ml). The PCR primers used were, for the 5' end of the IL-2 open reading frame, (SEQ ID NO:3)
5'-CCT CAA CTC CT*G AAT TC*A TGT ACA GGA TGC-3';

and for the 3' end of the IL-2 open reading frame, (SEQ ID NO:4)
5'-GGA AGC *GGA TCC* TTA TCA AGT CAG TGT TGA G-3'.

Restriction enzyme sites Eco RI (5'-end) and Bam HI (3'-end) were incorporated into each oligonucleotide and are indicated by italics. The PCR conditions used were 1 minute at 94° C., 1 minute at 58.7° C., and 1 minute at 72° C. for 25 cycles. The correct IL-2cDNA sequence so obtained was confirmed by sequencing using the Sequenase® sequencing kit (Amersham Life Sciences, Arlington Heights, Ill.) as described by the manufacturer. Uracil-containing single strand DNA (U-DNA) was obtained by transforming the *E. coli* strain CJ236 (Bio-Rad Laboratories, Hercules, Calif.) with IL-2cDNA-containing M13 mp19. Site-directed mutagenesis utilized in general primers containing 15 nucleotides homologous to the template U-DNA 5' to the codon(s)

targetted for mutagenesis, nucleotides that incorporate the desired change, and an additional 10 nucleotides homologous to the template U-DNA 3' of the last altered nucleotide. Initially, site-directed mutagenesis was used to introduce a Nco I restriction site at the beginning of the mature sequence of human IL-2. The use of this restriction site incorporates an N-terminal methionine residue that will direct expression in the cytoplasmic space of *E. coli* using for example, the expression vector pET3d. The primer used for this purpose was:

5'-GCA CTT GTC ACA AAC ACC ATG GCA CCT ACT TCA AGT-3'    (SEQ ID NO:5)

Specific primers used to incorporate mutations at positions D20, N88, and Q126 were:

D20X:  5'-GGA GCA TTT ACT GCT GNN NTT ACA GAT G-3'    (SEQ ID NO:6)

N88X:  5'-GGG ACT TAA TCA GCN NNA TCA ACG TAA TAG-3'    (SEQ ID NO:7)

Q126X: 5'-GGA TTA CCT TTT GTN NNA GCA TCA TCT C-3'    (SEQ ID NO:8)

where NNN was replaced with an appropriate codon for Histidine (CAC) or Isoleucine (ATC) (at position D20), arginine (CGT), glycine (GGT), or isoleucine (ATC) (at position N88), or leucine (CTG) (at position Q126). Other mutations utilized a similar strategy and an appropriate codon for a given mutation. Primers were phosphorylated using T4 polynucleotide kinase (New England Biolabs, Beverly, Mass.) using the manufacturer's protocol. After annealing of the primer to the U-DNA template and extension with T7 DNA polymerase (Bio-Rad Laboratories, Hercules, Calif.), cells of the *E. coli* strain DH5α™ (GibcoBRL, Gaithersburg, Md.) were transformed with 5 µl of reaction mixture and plated in LB medium containing 0.7% agar. After incubation at 37° C., plaques were expanded by picking a single plaque and transferring to 2 mls of LB media and grown overnight at 37° C. Single strand DNA was isolated using an M13 purification kit (Qiagen, Inc., Chatsworth, Calif.) per manufacturer's protocol, and clones containing the desired mutation were identified by sequencing the single stranded DNA using the Sequenase(& sequencing kit (Amersham Life Sciences, Arlington Heights, Ill.) per manufacturer's protocol. IL-2mutein cDNA from Replicative Form DNA corresponding to plaques containing the correct mutated sequence was isolated using NcoI and Xba I, and subcloned to the plasmid vector pET3a (Stratagene, San Diego, Calif.)(Strat). The *E. coli* strain BL21 was transformed with mutein containing pET3a vector, and grown to an $ABS_{280}$ of between 0.60 and 1.0, at which time 0.4 mM IPTG to induce IL-2 mutein production was added.

Example 2

Extraction and Purification of IL-2 Muteins from *E. coli*.

Three hours post induction the cells were harvested by centrifugation at 10,000×g. The recombinant IL-2 muteins were renatured and purified by first dispersing the cells in 10 volume (vol./wet mass) sucrose/Tris/EDTA buffer (0.375M sucrose, 10 mM Tris/HCL pH 8.0, 1 mM EDTA). The dispersed cells were sonicated 3 times at 300 W with 30 seconds rest intervals in a ice bath, using a Missonix model XL2020 sonicator equipped with 1 inch standard probe. The sonicated material was then centrifuged at 17,000×g for 20 minutes at 4° C. The pellet, which should be white in color at this point, was washed by resuspension and centrifugation one time in sucrose/Tris/EDTA buffer, twice with Tris/EDTA buffer (50 mM Tris/HCL pH 8.0, 1mM EDTA), and finally resuspended in 10 vol. 0.1 M Tris/HCL, pH 8.0 buffer (sample is taken at this point for gel analysis) and centrifuged for 20 minutes at 17,000×g.

The pellet was dissolved by adding 3 volumes of 8 M guanidinum chloride in 0.1 M Tris/HCL (pH 8.0), and 0.1% (vol/vol) 2-mercaptoethanol. After incubation for 2 hours at room temperature, the sample was centrifuged for 20 minutes at 17,000×g. The resultant solution was dialysed for approximately 20 hours against 20 volume 10 mM Tris/HCL, pH 8.0, 1 mM EDTA at 4° C. The solution was centrifuged at 17,000×g for 20 minutes, adjusted to 0.1% trifluoroacetic acid, and filtered in a 0.22 micron filter unit. The solution was transferred immediately to a siliconized bottle and loaded onto a C8 column (Vydac 208TP54). IL-2 muteins were purified using a 20 minute linear gradient using 45–85% acetonitrile in 0.1% TFA. The concentration of the eluted protein was determined by A280 and amino acid analysis. The protein was then aliquoted (100 ML) in siliconized tubes and stored at −20 degrees celsius. Mutein so purified was typically a single band as observed by SDS-PAGE (silver stain), and was quantitated by amino acid analysis (accuracy typically >90%).

Example 3

T Cell Proliferation Assay

Peripheral blood mononuclear cells (PBMC) were isolated from approximately 100 mL of normal human blood (Irwin Memorial Blood Bank, San Francisco, Calif.) diluted 1:2 in cold Dulbecco's phosphate buffered saline ($Ca^{2+}$ and $Mg^{2+}$ free; DPBS). Ficoll-Paque (Pharmacia) is underlayed and the sample is centrifuged to isolate the PBMC, followed by extensive washes in cold DPBS. PHA blasts (activated T cells) were generated by resuspending cells in RPMI 1640 containing 10% fetal bovine serum (Hyclone), to which 1% (w/v) of each of the following is added: L-glutamine; non-essential amino acids; sodium pyruvate; and antibiotic-antimycotic (RPMI media) at a density of $1 \times 10^6$ cells/ml. Phytohemmaglutanin (PHA-P; Sigma) was added at a final concentration of 10 µg/mL, and cells were incubated at 37° C., 5% $CO_2$ for 3 days. Cells were harvested and washed two times in DPBS, resuspended in RPMI media and plated into 96-well flat bottom plates at a density of $1 \times 10^5$ cells/well in 200 µl with varying concentrations of IL-2 or mutein in RPMI media. Plates were incubated for 48 hrs at 37° C., pulsed with 1 µCi $^3$H-thymidine (DuPont NEN®, Boston, Mass.)/well for 6 hrs, harvested, and radioactivity was measured after harvesting cells onto glass fiber filters.

Example 4

NK Cell Proliferation Assay

Peripheral blood mononuclear cells (PBMC) were isolated from approximately 100 mL of normal human blood (Irwin Memorial Blood Bank, San Francisco, Calif.) diluted 1:2 in cold Dulbecco's phosphate buffered saline ($Ca^{2+}$ and $Mg^{2+}$ free; DPBS). Ficoll-Paque (Pharmacia) is underlayed and the sample is centrifuged to isolate the PBMC, followed by extensive washes in cold DPBS. NK cells were separated from other cells. The Miltenyi Biotec's NK cell isolation kit (Bergisch Gladbach, Germany; Cat# 465-01) is preferred for this purpose. The kit consists of two reagents, separation columns and a very powerful magnetic column support. The first reagent is a cocktail of hapten conjugated monoclonal CD3, CD4, CD19, CD33 antibodies of mouse IgG1 isotype. This is to deplete the PMBC of T cells, B cells and myeloid cells. It is envisioned that any suitable set of antibodies recognizing these cell types can be used. The second reagent consists of colloidal super-paramagnetic MACs microbeads conjugated to an anti-hapten antibody. Cells are resuspended in PBS with 0.5% bovine serum albumin and 2 mM EDTA (PBS/EDTA). The volume of the suspension is dependent on the number of cells used and is provided in a chart by Miltenyi Biotec. Typically, with a cell number of 2 to $5 \times 10^8$ PBMC, the cells are resuspended in 800 uL of the buffer and then 200 uL of each reagent is used. After incubation with the reagents, the cells are added to the column (resuspended in 2 mLs of buffer). The non-NK cells adhere to the magnet (depleted) and the NK cells are isolated and collected in the flow through. Cells are washed, resuspended in RPMI media (contains: RPMI 1640, to which 1% of each of the following is added: L-glutamine; non-essential amino acids; sodium pyruvate; antibiotic-antimycotic (all from Gibco/BRL, Gaithersburg, Md.); 10% fetal bovine serum (Hyclone)), and plated into 96-well flat bottom plates at a density of $1 \times 10^5$ cells/well in 200 μl. Cells were harvested and washed two times in DPBS, resuspended in RPMI media and plated into 96-well flat bottom plates at a density of $1 \times 10^5$ cells/well in 200 μl with varying concentrations of IL-2 or mutein in RPMI media. Plates were incubated for 48 hrs at 37° C., pulsed with 1 μCi $^3$H-thymidine (DuPont NEN®, Boston, Mass.)/well for 6 hrs, harvested, and radioactivity was measured after harvesting cells onto glass fiber filters.

Example 5

Muteins which Selectively Activate T Cells over NK Cells

Muteins were generated using site-directed mutagenesis (Kunkel et al (1987), *Methods Enzymol* 154: 367–382) at postions Asp-20, Asp-84, Asn-88, and Gln-126, and were expressed in *E. coli* using the pET-3a expression system as described by the manufacturer (Stratagene). Muteins were purified by recovery of inclusion bodies in guanidine-HCL, refolded, and chromatographed using HPLC, as previously described. The resulting protein appeared >95% pure by silver stained SDS-PAGE, and was analyzed for concentration and purity by amino acid analysis (AAA accuracies typically >90%). Muteins having appropriate activity were confirmed in sequence using mass spectrometry analysis. Muteins so purified were assayed in the T and NK cell assays previously described. Relative activities for IL-2 muteins in the T and NK cell assays are indicated in Table 1.

TABLE 1

Muteins evaluated for T cell-selective activity

| Mutein | relative activity T vs. NK cell | relative activity T cell | relative activity NK cell |
|---|---|---|---|
| wt IL-2 | 1 | 1.00000 | 1.00000 |
| D20 muteins | | | |
| D20A | 5 | 0.00024 | 0.00005 |
| D20H | 3900 | 0.37081 | 0.00009 |
| D20I | 7600 | 4.59635 | 0.00061 |
| D20K | 330 | 0.06301 | 0.00019 |
| D20L | 100 | 0.00063 | 0.00001 |
| D20M | 490 | 0.05372 | 0.00011 |
| D20N | 160 | 0.03000 | 0.00019 |
| D20Q | 100 | 0.03180 | 0.00032 |
| D20R | 33 | 0.00018 | 0.00001 |
| D20S | 170 | 0.06640 | 0.00038 |
| D20T | 1 | 1.00000 | 1.00000 |
| D20V | 10 | 0.00093 | 0.00009 |
| D20Y | 1000 | 0.06587 | 0.00007 |
| N88 muteins | | | |
| N88A | 50 | 0.50000 | 0.01 |
| N88E | 10 | 0.01172 | 0.00115 |
| N88F | 22 | 0.02222 | 0.001 |
| N88G | 980 | 8.33333 | 0.00853 |
| N88H | 3 | 0.00100 | 0.001 |
| N88I | 9600 | 0.98074 | 0.00010 |
| N88K | 3 | 0.00010 | 0.00032 |
| N88L | 4 | 0.00400 | 0.001 |
| N88M | 250 | 0.25000 | 0.001 |
| N88R | 6200 | 0.89730 | 0.00015 |
| N88S | 80 | 0.00200 | 0.16000 |
| N88T | 395 | 0.50000 | 0.001266 |
| N88V | 67 | 0.06670 | 0.001 |
| N88W | 1 | 0.00100 | 0.001 |
| N88Y | 8 | 0.00800 | 0.001 |
| Q126 muteins | | | |
| Q126A | 0.30 | 0.01743 | 0.05809 |
| Q126D | 240 | 0.14630 | 0.00061 |
| Q126E | 400 | 10.0000 | 0.02500 |
| Q126F | 32 | 0.87358 | 0.02749 |
| Q126G | 100 | 0.55556 | 0.00556 |
| Q126H | 0.03 | 0.02216 | 0.73875 |
| Q126I | 33 | 0.00100 | 0.00003 |
| Q126K | 1.0 | 1.00000 | 1.00000 |
| Q126L | 680 | 3.06186 | 0.00447 |
| Q126M | 9.1 | 19.94092 | 2.19298 |
| Q126N | 10 | 6.57895 | 0.64993 |
| Q126P | 3.0 | 0.00032 | 0.00011 |
| Q126R | 11 | 4.02695 | 0.36392 |
| Q126S | 33 | 0.03417 | 0.00103 |
| Q126T | 3.3 | 0.00010 | 0.00003 |
| Q126V | 330 | 1.00556 | 0.00302 |
| Q126W | 1.0 | 0.20000 | 0.20000 |
| Q126Y | 10. | 0.88500 | 0.08850 |

Activities of muteins are described in terms of the relative concentration of mutein required to give a 50% maximum response ($EC_{50}$) in comparison with the $EC_{50}$ of wt IL-2 in the same assay; in the case of multiple assays on the same mutein, the geometric mean of the values are listed. The $EC_{50}$ values for wt IL-2 ranged between ~10 pM and 150 pM in the T cell assay, and ~50 pM and ~200 pM in the NK cell assay. The ratio of T cell vs. NK cell activity of muteins is expressed as the relative activity of the mutein on T cells divided by the relative activity of mutein on NK cells. This ratio is determined for each mutein using only activity determined from given T and NK cell assays using cells from a single donor.

Mutein activities can be classed into 6 broad categories: 1) 1000-fold T cell selectivity; 2) 100-but<1000-fold T cell selectivity; 3) 10-but<100-fold T cell selectivity; 4) improved activity relative to IL-2 on T cells; 5) NK cell selectivity; 6) 10-fold selectivity for either T or NK cells.

Class 1: D20H, I, and Y; N88G, I, and R.
Class 2: D20K, L, M, N, Q, and S; N88M and T; Q126D, E, G, L, and V.
Class 3: D20R; N88A, E, F, S and V; Q126F, I, N, R and S.
Class 4: D20I; N88G; Q126E, L, M, N, and R.
Class 5: Q126A, H.
Class 6: D20A, T, and V; N88H, K, L, W, and Y; Q126K, P, T, W, and Y.

Within Classes 1–3, preferred muteins are those that exhibit near wt IL-2 or better activity on T cells. In Class 1, this would include D20H and I; N88G, I, and R; in Class 2, this includes N88M and T, Q126D, E, G, L and V; in Class 3, this includes N88A, Q126F and G. Muteins in Class 4 are predicted to have greater potency than wt IL-2 in vivo.

It can be seen from Table 1 that no single mutation resulted in an IL-2 mutein inactive in both assays. However, it can be derived that a combination of mutations that resulted in severely compromised activity from two different positions would potentially yield an antagonist IL-2 activity on T cells, or other high affinity IL-2 receptor bearing cell types. Such an antagonist is predicted from this data as the mutations have been designed to alter only interactions with IL-2Rβ and IL-2Rγ. One such example would be the double mutein D20R/Q126T. The combination of weakly active mutations in one molecule is predicted to be combinatorial in nature, that is, D20R has 0.00018 activity on T cells, Q126T 0.0001 activity on T cells, the double mutein D20R/Q126T would be expected to have 0.000000018 the activity of wt IL-2 on T cells. Other combinations can be derived from the data provided.

Example 6

Biological Activity of wt IL-2 and IL-2 Muteins

FIGS. 1 to 7 show the dose-response curves of wt human IL-2 (IL-2) and D20H (FIG. 1), IL-2 and D201 (FIG. 2), IL-2 and N88G (FIG. 3), IL-2 and N88I (FIG. 4), IL-2 and N88R (FIG. 5), IL-2 and Q126E, (FIG. 6), and IL-2 and Q126L (FIG. 7). A: Individual dose response of IL-2 (closed circles) and mutein (open circles) in the primary human T cell proliferation assay (PHA-blasts). B: Individual dose response of IL-2 (closed triangles) and mutein (open triangles) in the primary human NK cell proliferation assay.

Particularly with respect to FIG. 1, for the experiment shown, the dose of wt IL-2 that gives 50% maximal proliferation ($EC_{50}$) is ~$1.5\times10^{-10}$ M for the T cell (A) and ~$1\times10^{-10}$ M for the NK cell (B) assay. The $EC_{50}$ for D20H was ~$2\times10^{-10}$ M in this T cell assay, but estimated to be >$1\times10^{-5}$ M in this NK cell assay. The net improvement in T cell activity of D20H over NK cell activity is thus >50,000-fold as determined for this assay. Similar results were obtained with blood from additional donors (data not shown).

Particularly with respect to FIG. 2, for the experiment shown, the dose of wt IL-2 that gives 50% maximal proliferation ($EC_{50}$) is ~$1.5\times10^{-10}$ M for the T cell (A) and ~$3\times10^{-10}$ M for the NK cell (B) assay. The $EC_{50}$ for D20I was also ~$1.5\times10^{-10}$ M in this T cell assay, but estimated to be only ~$5\times10^{-6}$ M in this NK cell assay. The net improvement in T cell activity of D20I over NK cell activity is thus −16,000-fold as determined for this assay. Similar results were obtained with blood from additional donors (data not shown).

Particularly with respect to FIG. 3, for the experiment shown, the dose of wt IL-2 that gives 50% maximal proliferation ($EC_{50}$) is ~$4\times10^{-11}$ M for the T cell (A) and ~$2\times10^{-10}$ M for the NK cell (B) assay. The $EC_{50}$ for N88G was ~$5\times10^{-12}$ M in this T cell assay, but estimated to be only ~$3\times10^{-8}$ M in this NK cell assay. The net improvement in T cell activity of N88G over NK cell activity is thus ~1,200-fold as determined for this assay. Similar results were obtained with blood from additional donors (data not shown).

Particularly with respect to FIG. 4, for the experiment shown, the dose of wt IL-2 that gives 50% maximal proliferation ($EC_{50}$) is ~$1.5\times10^{-10}$ M for the T cell (A) and ~$1\times10^{-10}$ M for the NK cell (B) assay. The $EC_{50}$ for N88I was ~$4\times10^{-10}$ M in this T cell assay, but estimated to be only ~$5\times10^{-6}$ M in this NK cell assay. The net improvement in T cell activity of N88I over NK cell activity is thus ~18,000-fold as determined for this assay. Similar results were obtained with blood from additional donors (data not shown). Similar results were obtained with blood from additional donors (data not shown).

Particularly with respect to FIG. 5, for the experiment shown, the dose of wt IL-2 that gives 50% maximal proliferation ($EC_{50}$) is ~$1.5\times10^{-10}$ M for the T cell (A) and ~$1\times10^{-10}$ M for the NK cell (B) assay. The $EC_{50}$ for N88R was ~$9\times10^{-11}$ M in this T cell assay, but estimated to be only ~$3\times10^{-7}$ M in this NK cell assay. The net improvement in T cell activity of N88R over NK cell activity is thus ~5,000-fold as determined for this assay. Similar results were obtained with blood from additional donors (data not shown).

Particularly with respect to FIG. 6, for the experiment shown, the dose of wt IL-2 that gives 50% maximal proliferation ($EC_{50}$) is ~$8\times10^{-12}$ M for the T cell (A) and ~$5\times10^{-11}$ M for the NK cell (B) assay. The $EC_{50}$ for Q126E was ~$8\times10^{-13}$ M in this T cell assay, but estimated to be only ~$2\times10^{-9}$ M in this NK cell assay. The net improvement in T cell activity of Q126E over NK cell activity is thus ~400-fold as determined for this assay. Similar results were obtained with blood from additional donors (data not shown).

Particularly with respect to FIG. 7, for the experiment shown, the dose of wt IL-2 that gives 50% maximal proliferation ($EC_{50}$) is ~$5\times10^{-11}$ M for the T cell (A) and ~$8\times10^{-11}$ M for the NK cell (B) assay. The $EC_{50}$ for Q126L was ~$2\times10^{-11}$ M in this T cell assay, but estimated to be only ~$2\times10^{-8}$ M in this NK cell assay. The net improvement in T cell activity of Q126L over NK cell activity is thus ~625-fold as determined for this assay. Similar results were obtained with blood from additional donors (data not shown).

Example 7

Chimpanzee Toxicity Studies

IL-2/N88R was selected from the IL-2 mutant proteins in Table 1 because of its demonstrated T-cell selective agonist activity in primary human T and NK cell assays. Relative to wild-type IL-2, it is ~6,000-fold more active on T cells than NK cells, and exhibits activity essentially equivalent to wt IL-2 on T cells. IL-2/N88R was produced in CHO cells, purified, and evaluated in a chimpanzee model of IL-2 activity and toxicity. In this in vivo model, it exhibited T cell activity comparable to a commercially-available recombinant variant of IL-2 (PROLEUKIN™, Chiron Corporation, Emeryville, Calif.), yet induced only mild side-effects in comparison (both in terms of objective and clinical parameters).

A. Experimental Design

1. Materials and Methods

The in-life portion of the study took place at New Iberia Research Center (New Iberia, La., Sponsor Bayer Corporation, Berkeley, Calif.) and involved two phases of studies and 11 young adult to adult male chimpanzees with body weights that ranged from about 45 to 70 kg.

Phase I of the study was a dose determination phase and involved delivering a subcutaneous dose of a vehicle or a subcutaneous dose of PROLEUKIN at 1.2 mg/m$^2$, twice daily (BID) for 5 days. Phase II of the study is a comparison of the vehicle, PROLEUKIN, and IL-2/N88R given subcutaneously, every 12 hours (q12 h) for 5 days. The dose of IL-2/N88R was selected to provide comparable exposure to PROLEUKIN based upon pharmacokinetic analysis. Blood samples were taken for analyses of blood chemistry, CBC, hematology/coagulation, and FACS analysis of T and NK cell populations as detailed in Sections 5 and 6.

TABLE 2A

Phase I Protocol

| Group Number | Number of Animals | Test Article | Dose | Frequency |
|---|---|---|---|---|
| 1 | 1 | Vehicle | NA | BID for 5 days |
| 2 | 2 | PROLEUKIN | 1.2 mg/m$^2$ | BID for 5 days |

TABLE 2B

Phase II Protocol

| Group Number | Number of Animals | Test Article | Dose | Frequency |
|---|---|---|---|---|
| 1 | 2 | Vehicle | 2.4 ml/m$^2$ | q12 h for 5 days |
| 2 | 3 | PROLEUKIN | 1.2 mg/m$^2$ | q12 h for 5 days |
| 3 | 3 | IL-2/N88R | 1.2 mg/m$^2$ | q12 h for 5 days |

2. Dosing Procedure

On study days in which blood was to be obtained, animals were completely anesthetized using IM ketamine at a dose of approximately 10 mg/kg prior to administration of the test article or vehicle. On study days in which blood sampling was not required, animals were physically restrained using a squeeze cage prior to administration of the test article or vehicle. The dose was administered by subcutaneous injection every 12 hours for 5 days, and the injection site was clipped of hair on Day 1 of the study. The site and time of dosing was recorded for each dose.

3. Clinical Observations (a) Daily Observations and Food Consumption. Each animal was observed twice daily and any abnormal observation was reported to the Study Director. Animals appearing ill were brought to the attention of the Study Director, Project Veterinarian, and the Sponsor Representative. Food consumption was confirmed and recorded twice daily by visual observation.

(b) Body Weights. Body weights were taken pre-study, prior to dosing on day 1, and each time the animals were sedated for blood collection.

(c) Observation of Injection Sites. Injections sites were observed daily. Any abnormal appearances such as redness or swelling was recorded.

TABLE 3A

Schedule for Phase II sample collection

| Time | CBC | CHEM | COAG | FACS | SPONSOR ASSAY |
|---|---|---|---|---|---|
| Pre-study | X | X | X | X | X |
| Day 1, pre-dose | X | X | X | X | X |
| Day 1, 15 min | | | | | X |
| Day 3, pre dose | X | X | X | X | X |
| Day 3, 15 min | | | | | X |
| Day 6 | X | X | X | X | X |
| Day 8 | X | X | X | X | X |
| Day 10 | X | X | X | X | X |
| Day 12 | X | X | X | X | X |
| Day 15 | X | X | X | X | X |
| Day 30 | X | X | X | X | X |

4. Sample Handling (a) Serum Chemistries. Approximately 2 ml blood samples were collected from each animal into tubes without anticoagulant at the above specified time points. Blood collection times were documented and blood was allowed to clot at room temperature. The samples were then centrifuged, the serum separated and forwarded to the NIRC Clinical Pathology Laboratory. The NIRC standard serum chemistry panel included in Table 4:

TABLE 4

Blood chemistry panel

| | |
|---|---|
| Sodium | Phosphorus |
| Potassium | Urea Nitrogen |
| Chloride | Creatinine |
| Total Bilirubin | Total Protein |
| Alkaline Phosphatase | Albumin |
| Lactate Dehydrogenase (LDH) | Albumin/Globulin Ratio |
| Aspartate Aminotransferase (AST) | Glucose |
| Alanine Aminotransferase (ALT) | Calcium |
| Carbon Dioxide (CO$_2$) | Gamma-glutamyl transferase (GGT) |

(b) Hematology. Approximately 2 ml blood samples was collected from each animal into EDTA tubes at the above specified time points and forwarded to the NIRC Clinical Pathology Laboratory. The standard NIRC hematology panel, including complete blood count, differential, and platelet count, was run on all samples.

(c) Sponsor Assays. Approximately a 6 ml blood sample was collected into tubes with EDTA as an anticoagulant at the times specified above. Blood collection times were documented. The samples were centrifuged, the plasma separated and aliquoted into three separate tubes. The plasma was stored frozen (−60° C. or below) and shipped to Bayer Corporation, Berkeley, Calif. as soon as the study was completed.

5. FACS (a) Procedure. Approximately a 5 ml blood sample was collected in sodium heparin anticoagulant at the times specified for FACS analysis.

Whole blood specimen was obtained in either EDTA, ACD or heparin. Cell numbers were adjusted to be in the range of 2 to 20 thousand per mm3.

12×75 glass or plastic tubes were appropriately labeled for the antibody panel being run. Antibody or antibody cocktail were added to the tubes following manufacturer suggested volumes.

100 μl of well-mixed blood specimen was added per tube and the mixture was incubated for 30 mn at room temperature, protected form light.

After incubation, 2 ml of lysing solution (Becton Dickinson FACS brand lysing solution, BD#92-0002) were added, the mix was vortexed gently and let stand for 10 minutes at room temperature. The tubes when then centrifuged at room temperature for 5 minutes at 300×g. Supernatants were decanted, excess liquid blotted and 1 ml of PBS buffer (GIBCO 14190-144) was added to each cell pellet. After a gentle vortex, the tubes were centrifuged at room temperature for 5 mn at 300×g. Supernatants were decanted and excess liquid blotted before adding 1 ml of fixative solution (0.5% formaldehyde solution, prepared by diluting 10% formaldehyde (Polyscience, Inc. #0418) 1:20 with PBS buffer) on the cell pellet and vortexing gently for resuspension. Samples were then analyzed on a Coulter EPICS SL Flow Cytometer.

Antibodies used for the study: MIgG1/MIgG1 isotype control (Becton Dickinson, Cat. #349526), CD45-PerCP (Becton Dickinson, Cat. #347464), CD8-FITC (Becton Dickinson, Cat. #347313), CD25-PE (Becton Dickinson, Cat. #30795X), CD4-FITC (Becton Dickinson, Cat. #340133), CD16-PE (Pharmingen, Cat. #347617), CD3-PerCP (Becton Dickinson, Cat. #347344).

6. Coagulation Profile

Approximately a 2 ml whole blood sample was collected into tubes with sodium citrate added as an anticoagulant at the above specified time points. The coagulation profile consisted of Prothrombin Time (PT), Activated Partial Thromboplastin Time (APTT) and Fibrinogen.

B. Results And Discussion

1. PROLEUKIN Dose Determination

The primary goal of this phase was to identify an optimal PROLEUKIN dose for comparison with IL-2/N88R. This optimal dose of PROLEUKIN was targeted to be a tolerable dose (lower than the maximum tolerated dose) which will ideally cause clinically significant, but moderate and reversible toxicity. A PROLEUKIN dose of 1.2 mg/M$^2$, BID, was determined as the initial dose based on cross-species extrapolation given clinical dose regimens of PROLEUKIN, their corresponding toxicities, and in-house cynomolgus monkey PROLEUKIN dose-response results.

Figures 8A, 8B, 8C, 8D:
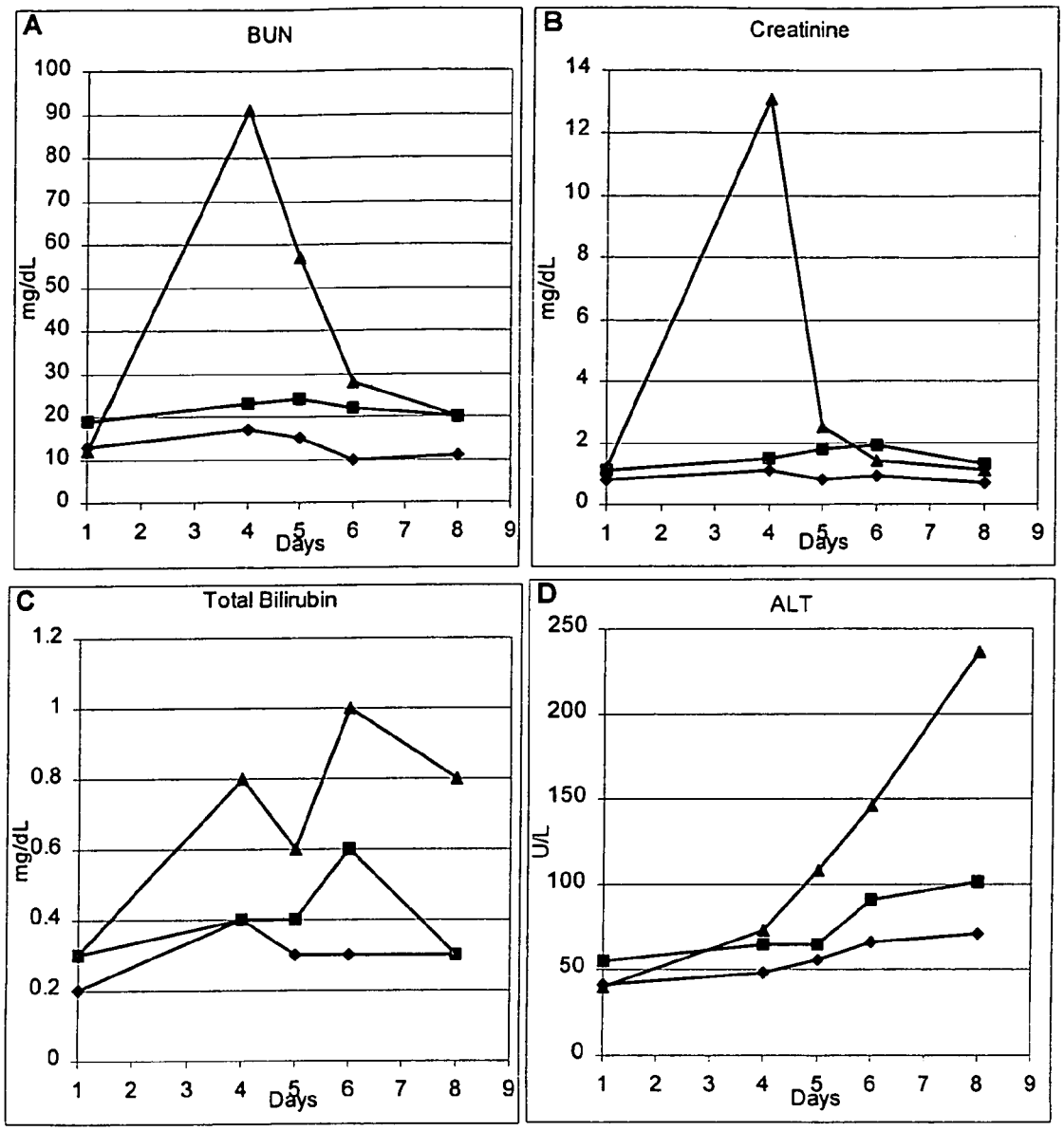

Two chimpanzees were treated in this manner with PROLEUKIN. These animals became increasingly less active, distressed, and dehydrated throughout the course of dosing. Both animals developed severe gastrointestinal symptoms starting on days 3 or 4, including reduced appetite, diarrhea, vomiting. Dosing on one animal (number X-159) was discontinued after 3 days of dosing because of severe renal (FIG. 8A & B) and moderate hepatic (FIG. 8C & D) dysfunction reflected in blood chemistry chemistries. These include elevations of blood urea nitrogen (BUN), creatinine, and total bilirubin, ALT (SGPT). Lactated Ringers solution was given i.v. to both PROLEUKIN-treated animals on day 3 and 4 (animal X-159) and day 4 only (animal X-124) as resuscitation or to prevent further dehydration. Animal number X-159 was removed from the study on day 8 due to renal dysfunction and possible thrombus on the right leg as indicated by very minimal pulse (femoral), and the entire calf was cold and enlarged. Although significant toxicity was observed in one animal, the other animal experienced less severe events and the profile of adverse events for both animals was reversible. Based on this, 1.2 mg/M$^2$ PROLEUKIN and the equivalent dose (based on exposure) of IL-2/N88R, q12 hr was determined to be an appropriate dose regimen to compare these two compounds.

2. Comparison of IL-2/N88R to PROLEUKIN

Figure 9:
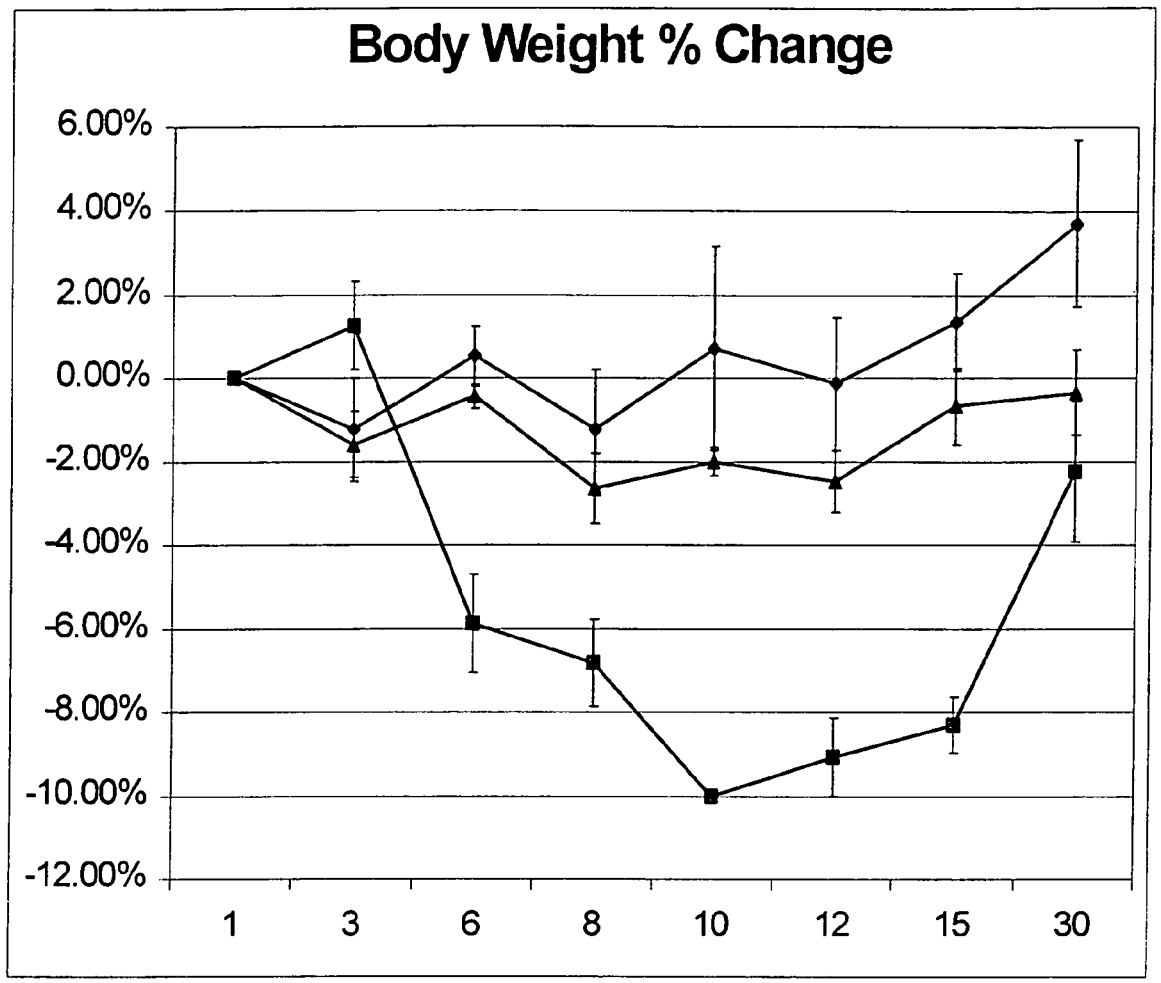

Clinical Observations. Table 5 lists the clinical observations made during the study. Values are reported on a scale of 0 to 5, where 5 is severe. All PROLEUKIN treated animals were severely ill; there was one PROLEUKIN treatment-associated death. Values reported post day 6 for the PROLEUKIN group reflect data from the remaining two animals. The most obvious side-effect of IL-2/N88R treatment appeared to be mild GI disturbance (emesis) although treatment did induce nominal toxicity in terms of the parameters indicated in Table 4. Body weight of the PROLEUKIN group fell 6% on day 6 and dropped as low as 10% on day 10 and slowly recovered thereafter (see FIG. 9). In contrast, IL-2/N88R and the vehicle groups had merely 1–3% weight loss at most.

TABLE 5

Clinical observations*

| Treatment | General Condition | Loss of Appetite | Lethargy | GI | Malaise |
|---|---|---|---|---|---|
| IL-2/N88R | good | 1 | 1 | 2 | 1 |
| PROLEUKIN | severely ill | 5 | 4/5 | 5 | 4/5 |
| Vehicle | normal | 0 | 0 | 0 | 0. |

Figures 10A, 10B, 10C, 10D:
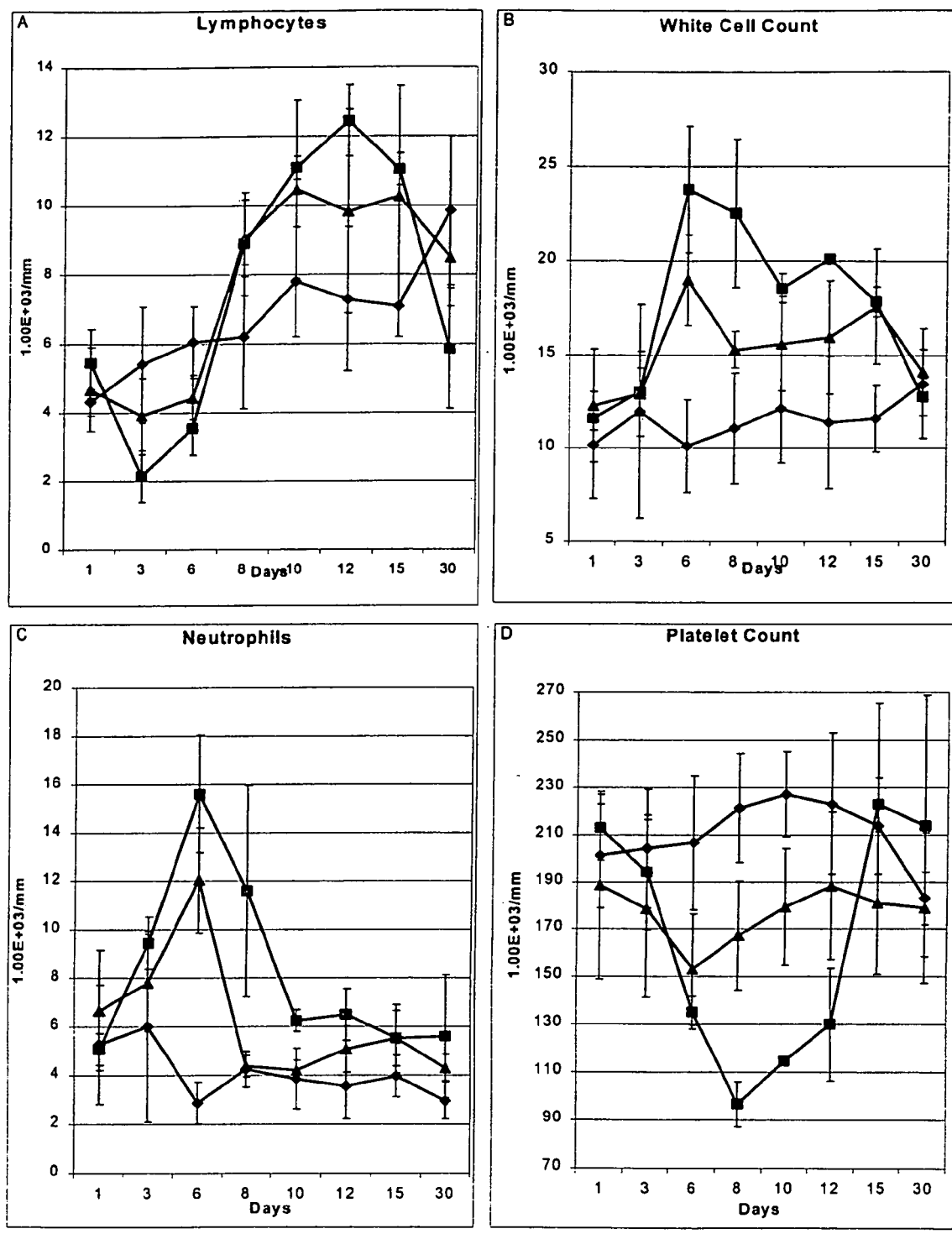

*Scale of 0 to 5, where 5 is most severe (a) Hematology. IL-2/N88R induced cellular effects consistent with PROLEUKIN activation, in particular lymphocytosis (FIG. 10A), increase in white blood cells (FIG. 10B) and neutrophils (FIG. 10C.) were also observed. IL-2/N88R induced only a marginal thrombocytopenia (nadir of ~15%) compared to PROLEUKIN (nadir ~50%) during the treatment portion of the study (FIG. 10D).

Figures 11A, 11B, 11C, 11D:
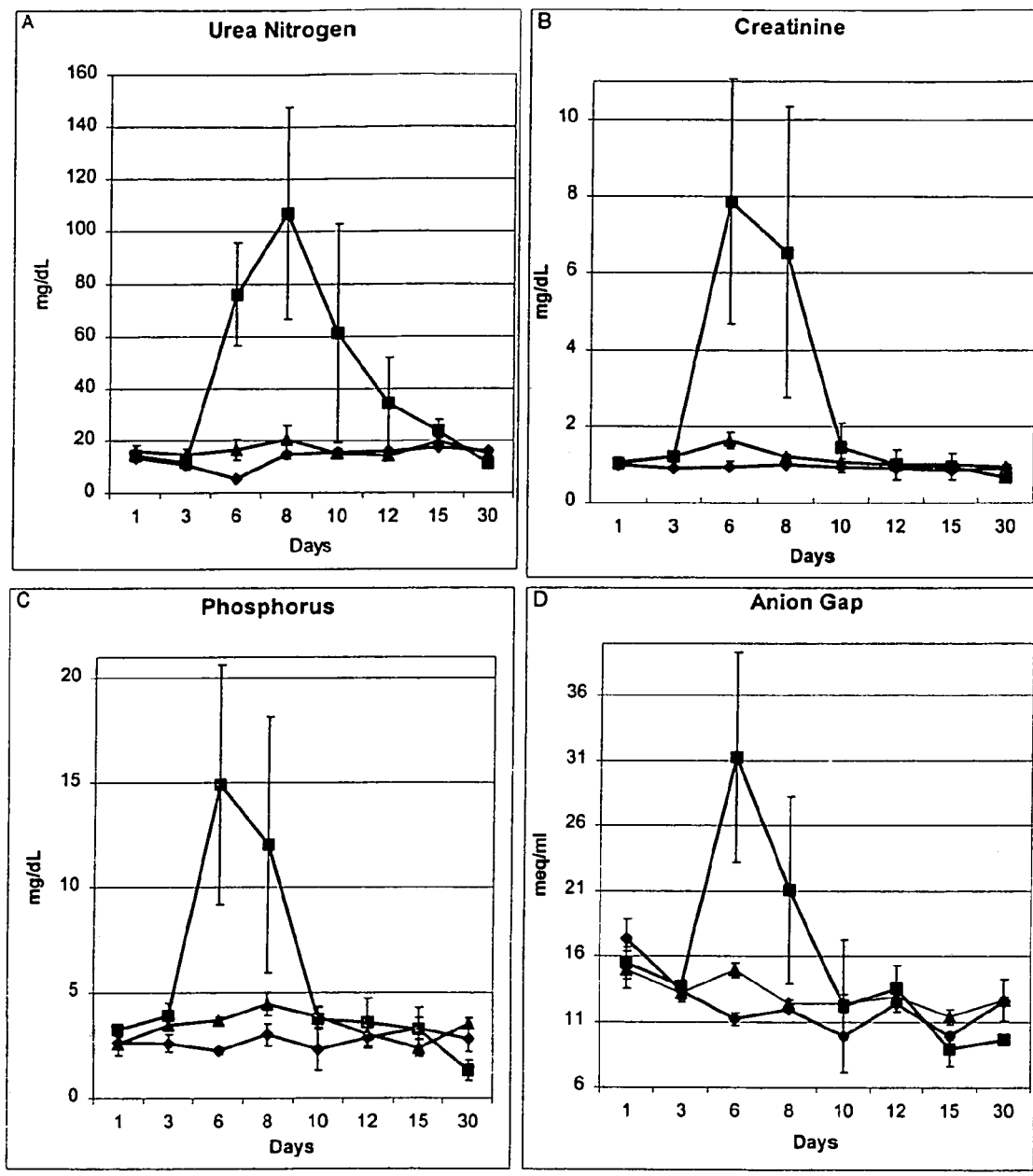

(b) Renal Function. BUN levels were markedly higher in all Proelukin treated animals on days 6 and 8 (FIG. 11A). BUN levels were over 130 mg/dL in two of these animals; Creatinine levels also increased dramatically in the two animals on both day 6 and day 8 (FIG. 11B) indicating a complete shut down of renal function. In addition, both serum phosphorus and anion gap also increased in the PROLEUKIN treated group on days 6 and 8. In contrast, in all IL-2/N88R animals, these renal parameters remained basically normal throughout the study (FIG. 11C&D).

Figures 12A, 12B, 12C, 12D:
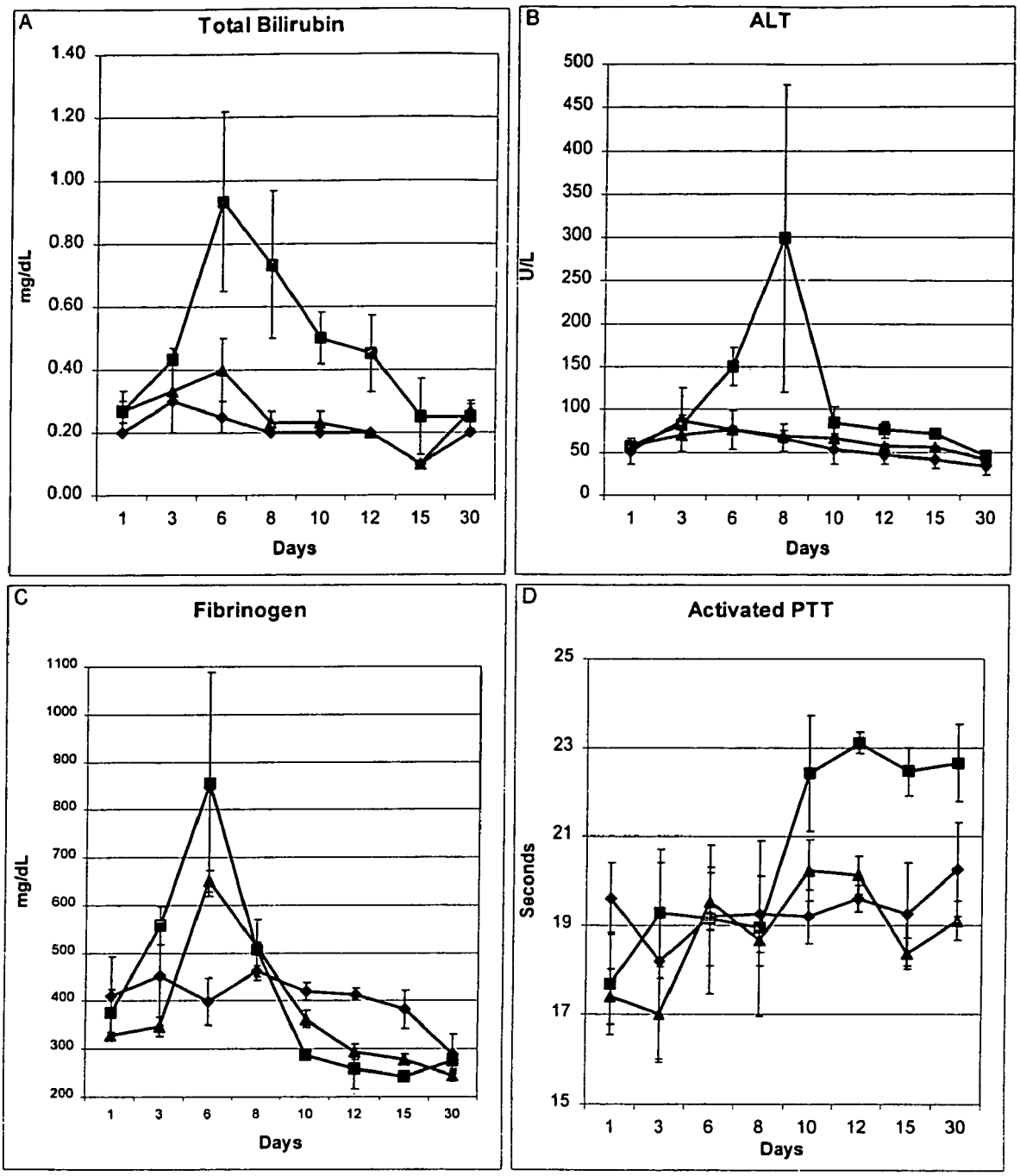

(c) Hepatic Function. Total bilirubin more than tripled in the PROLEUKIN group on day 6 and remained high through day 10 (FIG. 12A). In contrast, only one animal in the IL-2/N88R group had a transient, minor increase on days 3 and 6. Serum SGPT level elevated dramatically and reached over 100 U/L in all PROLEUKIN animals on day 6 (FIG. 12B). The SGPT level in animal number A199 reached 651 U/L, and the SGOT 2789 U/L (Lab Note Book: NIRC#8754-9852-Phase II, Table 1 Individual and Group Mean Chemistry Values, page 17 of 21 of the table), indicating a severe liver failure.

(d) Coagulation. Fibrinogen level more than doubled in both PROLEUKIN and IL-2/N88R groups and peaked on day 6 (FIG. 12C). The increase appears to have happened earlier in the PROLEUKIN group than the IL-2/N88R animals. This is reflected by an increase of 51% vs. 5% on day 3. The changes in fibrinogen may be a result of acute protein response rather than coagulation defects since there were no meaningful changes in APTT or PT accordingly during the same period of time (FIG. 12D). However, starting from day 10 the APTT level in PROLEUKIN animals showed an obvious up trend although the absolute value remained within the normal range. The same trend, although to a lesser extend, was also observed in the IL-2/N88R group. Interestingly, however, fibrinogen level appeared to have drifted lower during the same period of time accordingly in both groups.

Figures 13A, 13B, 13C, 13D:
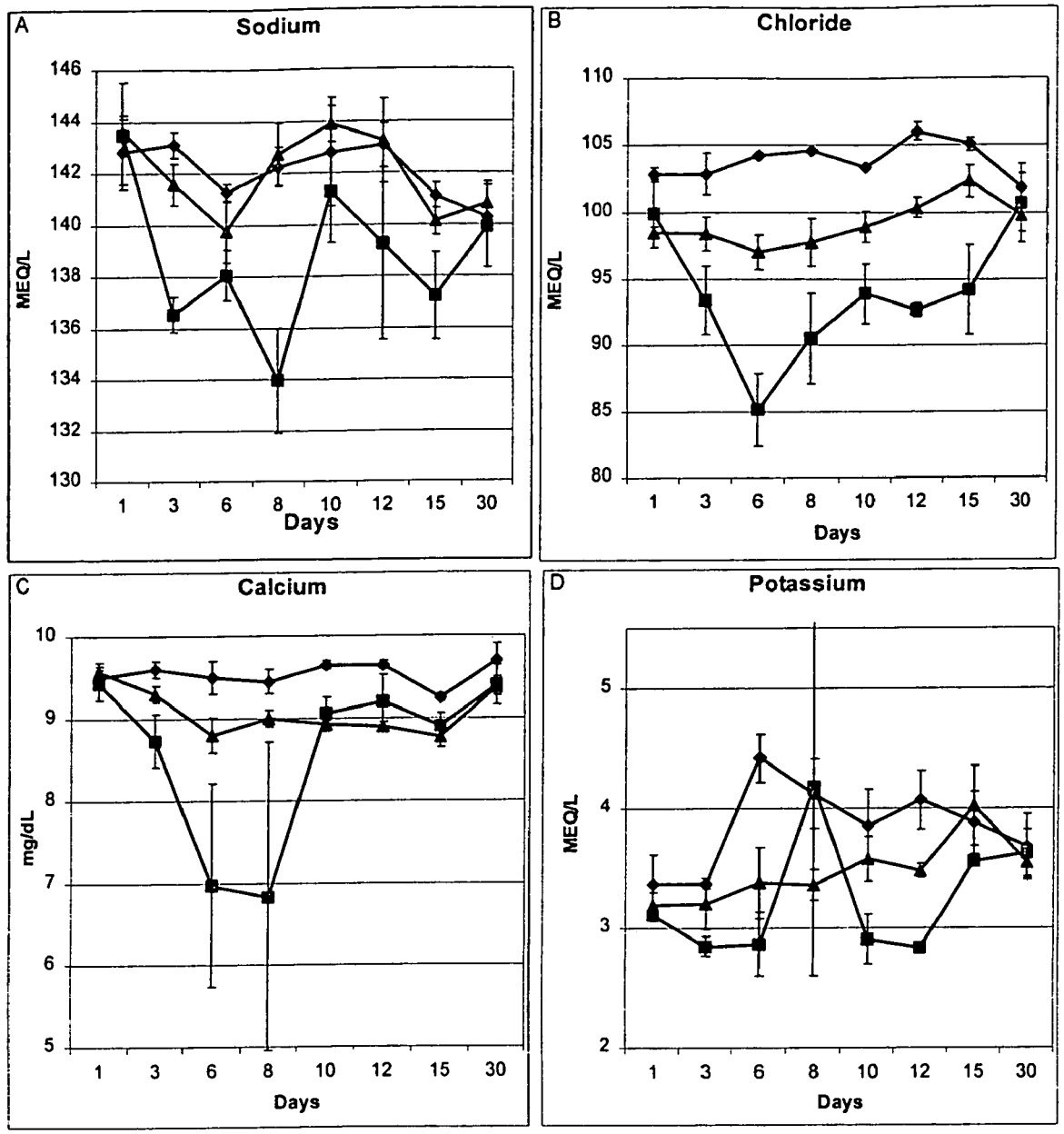

(e) Homeostasis. Serum sodium levels decreased to under 135 MEQ/L in two of the three PROLEUKIN animals on day 8, but remained normal in the rest of the animals (FIG. 13A). Chloride levels in the PROLEUKIN group were also reduced to under 95 MEQ/L starting on day 3 and remained low until day 15 (FIG. 13B). The calcium level was lower in two of three PROLEUKIN animals on days 6 and 8, and reached as low as 4.9 and 3.1 mg/dL in animal A199 (FIG. 13C). The potassium level decreased to under 3 MEQ/L from days 3 to 12 in all PROLEUKIN treated animals except animal Al199 whose potassium level actually increased to a toxic level of 7.2 MEQ/L before being taken off the study (FIG. 13D).

Figures 14A, 14B, 14C:
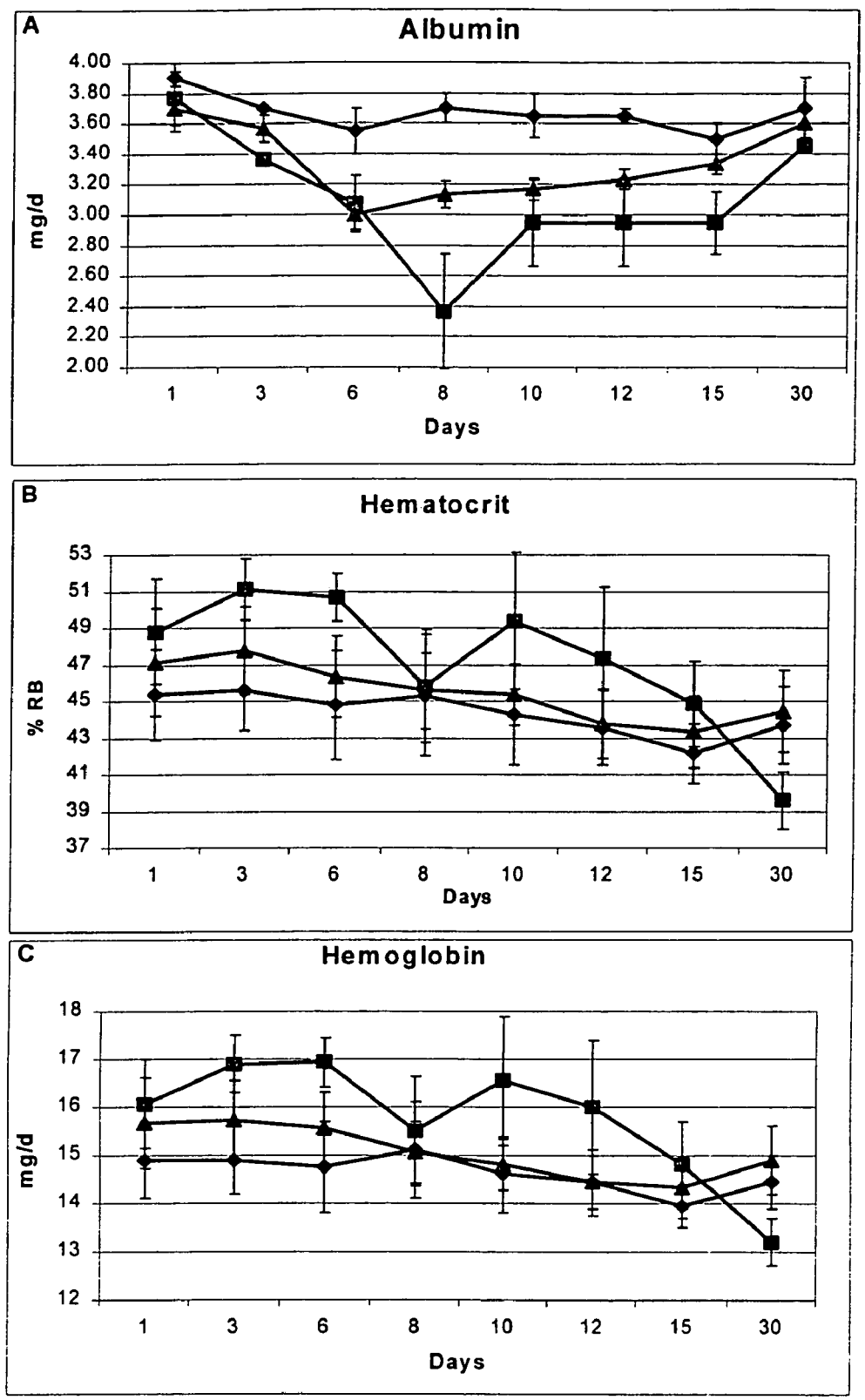

(f) Signs of Vascular Leak. Serum albumin level decreased in both PROLEUKIN (37%) and IL-2/N88R (19%) groups (FIG. 14A). An increase in hematocrit level was observed in the PROLEUKIN group on days 3 and 6 (FIG. 14B). In contrast, the hematocrit levels in both vehicle control and IL-2/N88R groups decreased during the same time period and remained low indicating mild anemia as expected due to multiple blood sample collections (FIG. 14B&C). The elevation of hematocrit in the PROLEUKIN group when coupled with a decrease in albumin is consistent with the development of capillary leak syndrome.

3. Cellular Activation.

PROLEUKIN and IL-2/N88R efficacy were followed through the variation of the percentage of CD25 positive lymphocytes (trafficking+proliferation) and the mean of fluorescence for CD25 or number of CD25 antigens expressed at the surface of a given T cell (CD25=low affinity IL-2R). CD25 expression was followed on the total T cell population (CD3+ cells) as well as the CD3+CD4+ and CD3+CD8+ populations.

IL-2 activity on Natural Killer cells (NK) was followed through an analysis of the trafficking of CD3-CD16+ and CD3-CD25+CD16+ NK cells. The absolute numbers of CD3+, CD4+, CD8+, NK cells were determined by multiplying the cells percentage by the number of lymphocytes per mm3, data obtained during the hematology analysis.

Figures 15A, 15B, 15C:
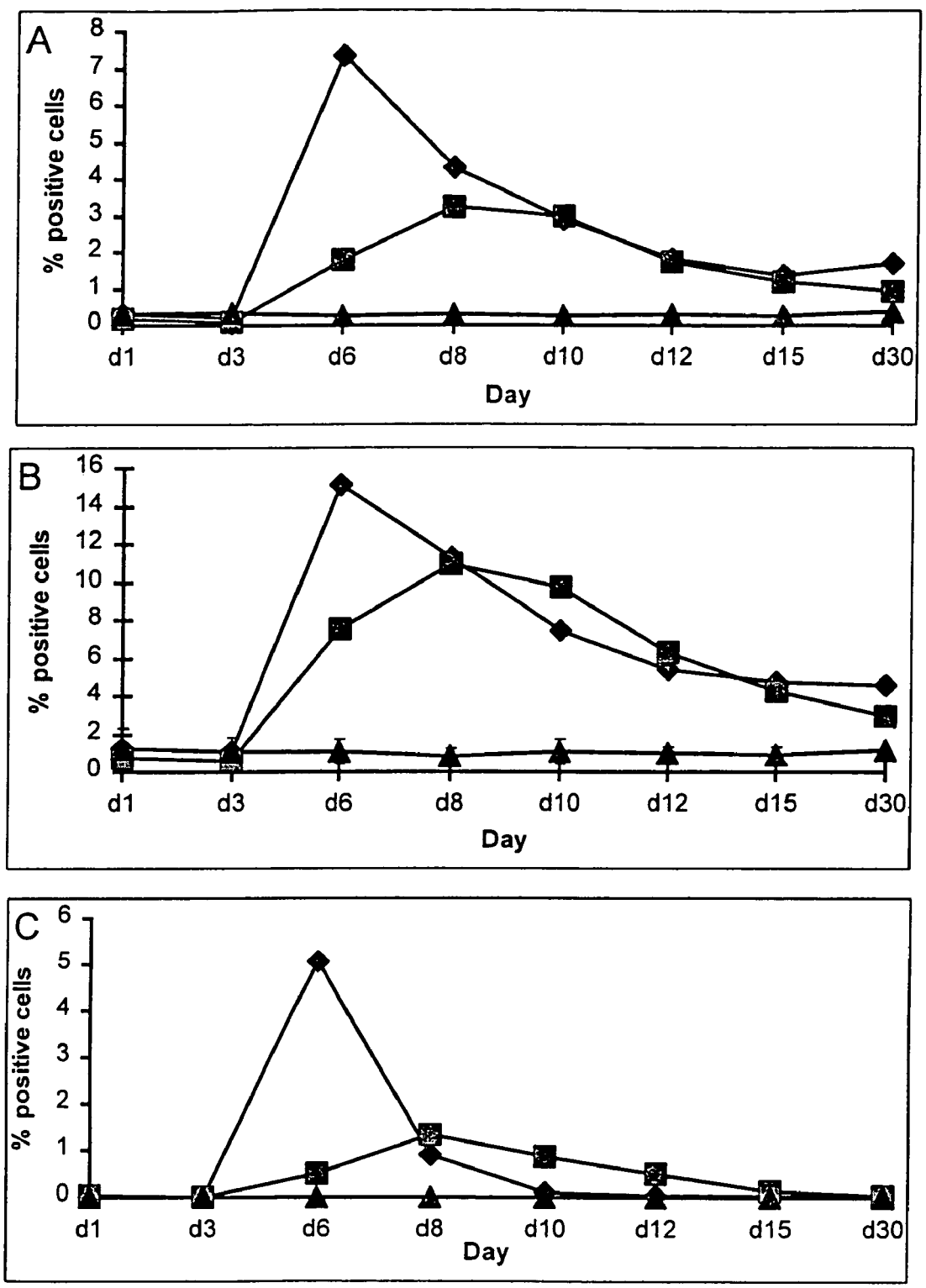

(a) CD25 regulation of expression on the T cell surface. The percentage of activated T cells, as indicated by CD25 positive cells, was up-regulated by day 6 of the study, mostly on the CD3+CD4+ T cell subpopulation. PROLEUKIN appears to induce the expression of CD25 on a higher percentage of total CD3+, CD3+CD4+ and CD3+CD8+ subpopulations of T cells at day 6. However by day 8 the percent of cells expressing the CD25 antigen was identical on the lymphocytes of chimpanzees treated by PROLEUKIN and the chimpanzees treated with IL-2/N88R(FIG. 15A, B and C). No staining for CD25 at the surface of the Natural Killer (NK) cell population was observed in either PROLEUKIN or IL-2/N88R treated chimpanzees. Lack of expression of IL-2Rα (the antigen targeted for cell surface staining by CD25) at the surface of the selected NK cell population (CD3−/CD 16+) is suspected to be responsible for these results.

Figures 16A, 16B, 16C:
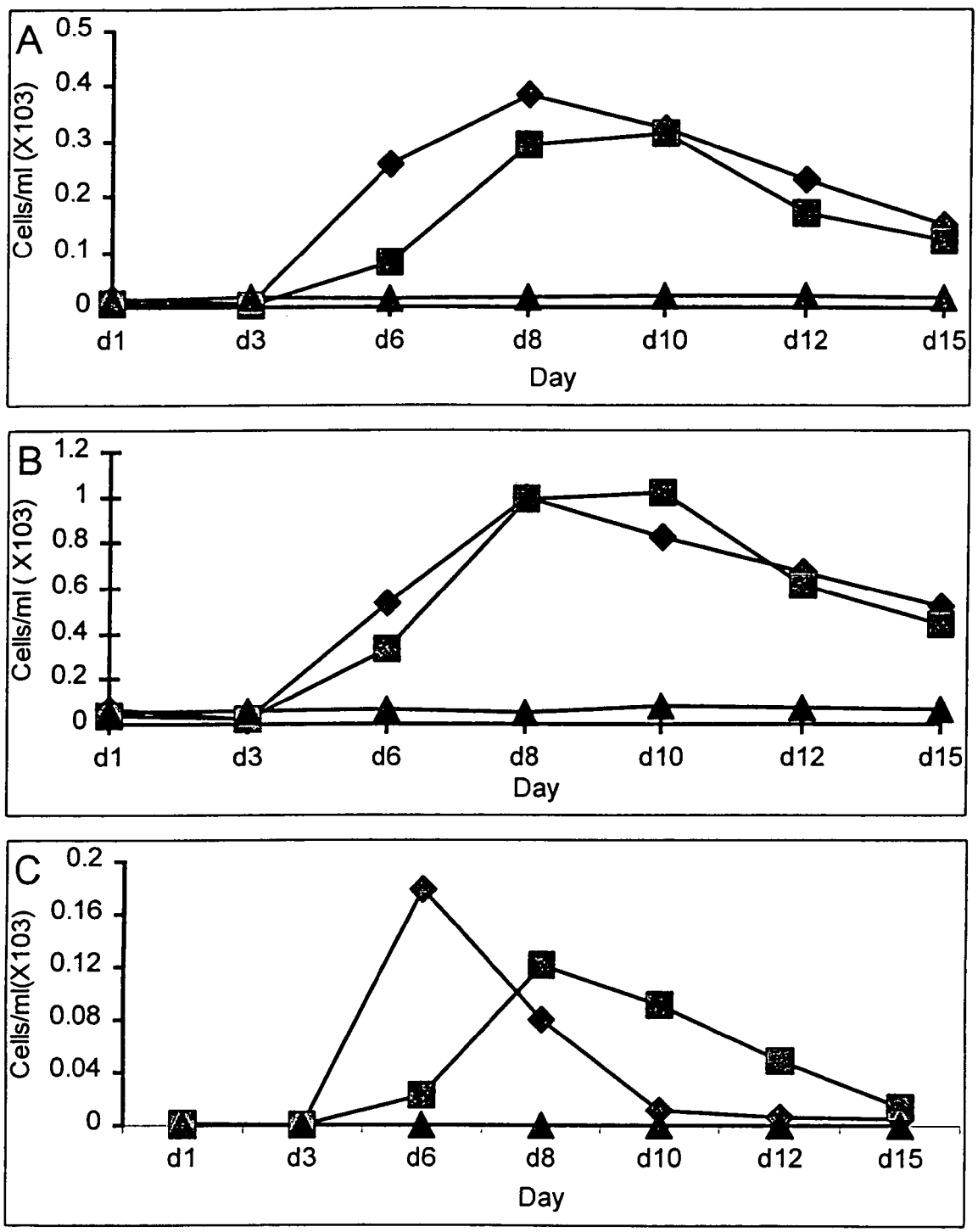

The absolute number of CD3+CD25+ T cells followed a similar pattern as the percentage of CD3+CD25+ T cells, with PROLEUKIN appearing more active than IL-2/N88R (FIG. 16A). IL-2/N88R exhibited a similar T cell activation potential as PROLEUKIN on the CD3+CD4+ T cell population, as the up-regulation of the absolute number of CD3+CD4+CD25+ lymphocytes induced by IL-2/N88R was identical to the up-regulation seen with PROLEUKIN (FIG. 16B). PROLEUKIN appeared to increase the number of CD3+CD8+CD25+ T cells to a greater extent than IL-2/N88R (FIG. 16C).

Figure 17:
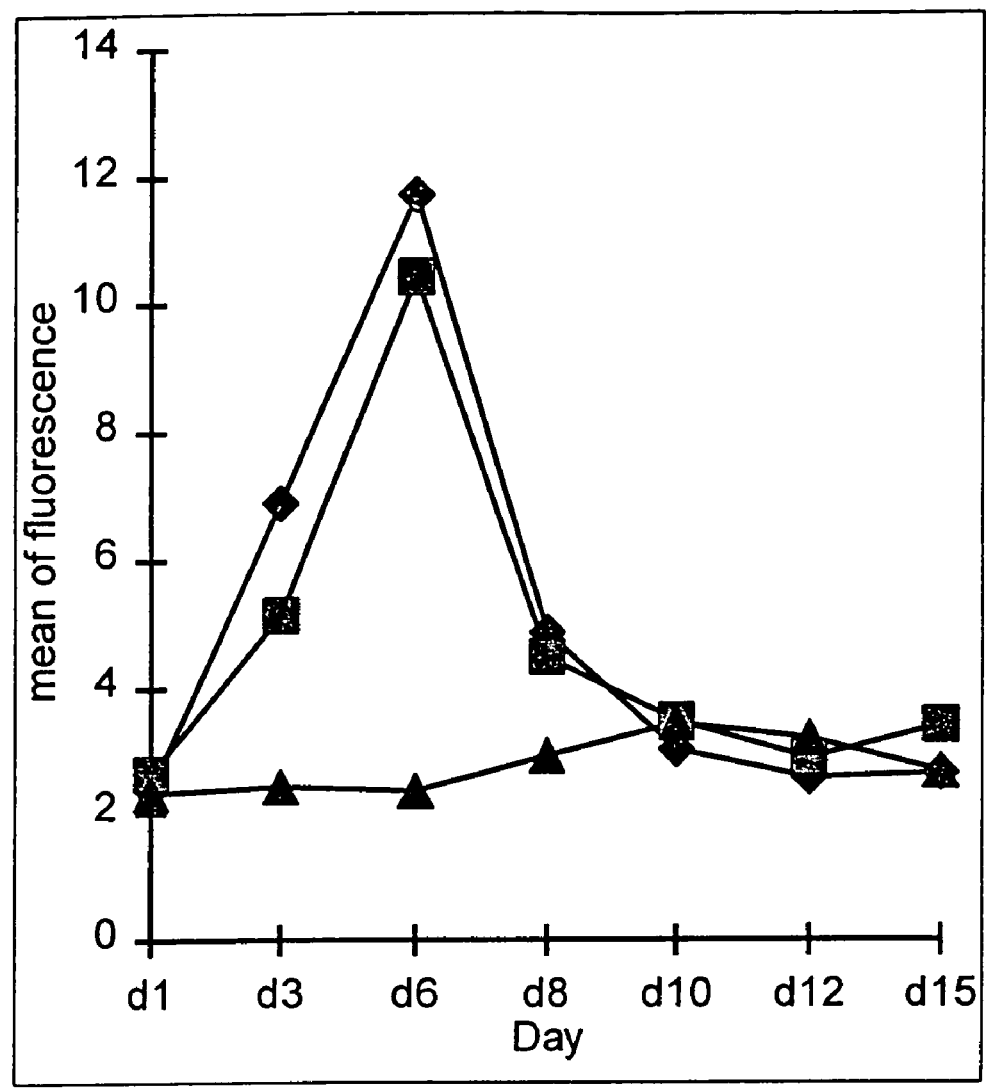

The number of CD25 molecules (mean of fluorescence) expressed on the CD3+CD4+ T cell subpopulation followed identical kinetics with either PROLEUKIN or IL-2/N88R treatment (FIG. 17).

Figures 18A, 18B, 18C, 18D:
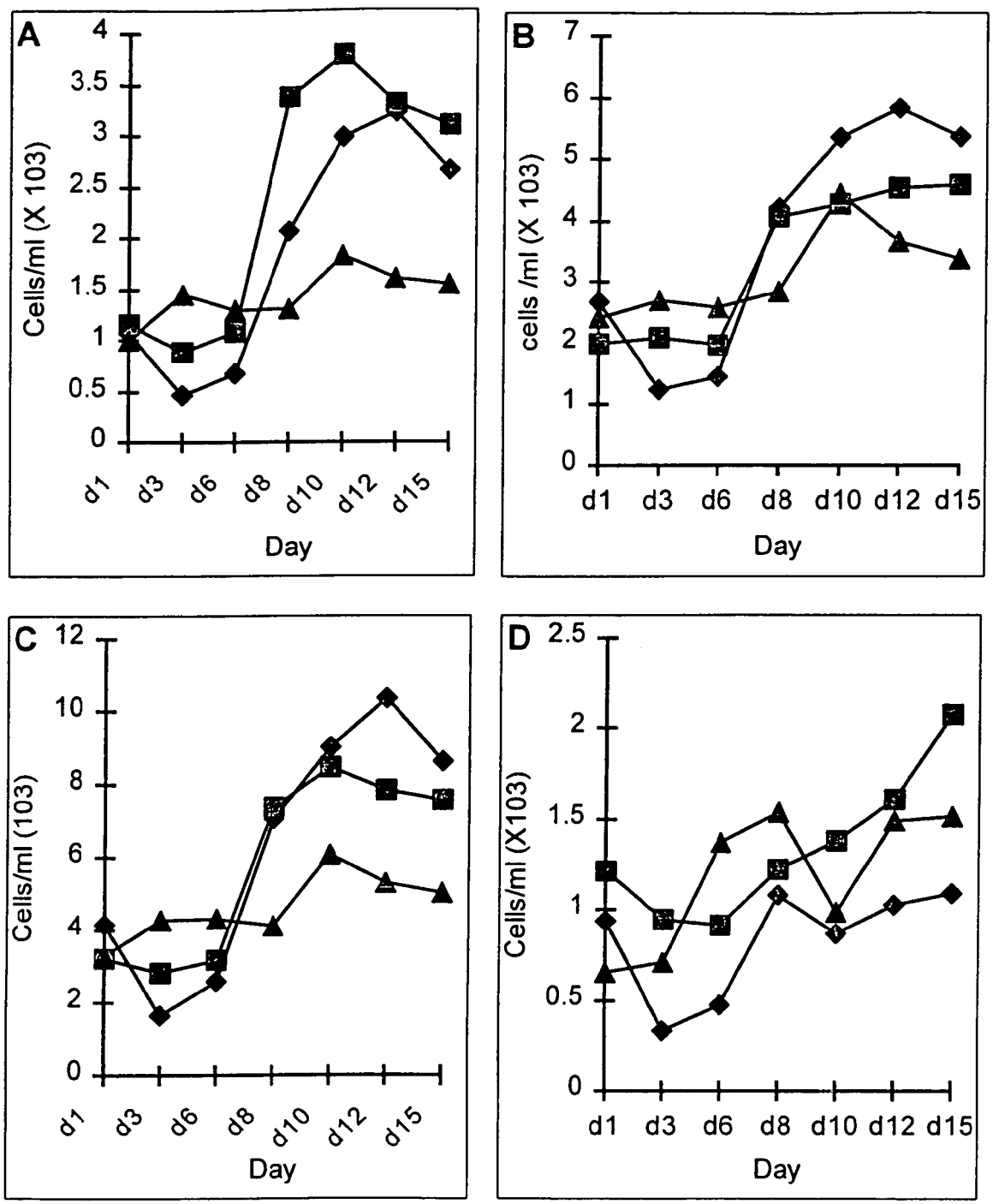

(b) Lymihocyte trafficking: effect of PROLEUKIN and IL-2/N88R treatment. PROLEUKIN and IL-2/N88R activities on the T and NK cell populations were determined through the analysis of the variation in the absolute number of circulating lymphocytes before, during and after treatment (FIG. 18). IL-2/N88R appeared to have a greater activity than PROLEUKIN for increasing the absolute number of CD3+CD4+ circulating lymphocytes (FIG. 18A), and a slightly reduced activity compared to PROLEUKIN for increasing the absolute number of CD3+CD8+ circulating lymphocytes (FIG. 18B). Both compounds had a comparable, though modest, effect on increasing the total number of CD3+ lymphocytes (FIG. 18C). Neither PROLEUKIN nor IL-2/N88R affected trafficking of NK cells (FIG. 18D).

C. Conclusion

IL-2/N88R was generated through a screen of mutant IL-2 proteins in human primary T and NK cell assays. It exhibits in vitro selectivity for T cells over NK cells of ~6,000-fold. Based on this cellular profile, it was postulated that it would only induce mild side effects when administered at a dose that would elicit significant T cell activation. Experiments in chimpanzee, comparing PROLEUKIN to IL-2/N88R, confirmed that IL-2/N88R has a significantly better safety profile than PROLEUKIN, while retaining comparable ability to induce T cell activation.

Example 8

Efficacy of IL-2 Selective Agonist N88R in the Murine CT-26 Lung Metastases Tumor Model Protocol: Mice (Balb/c, females, 6–8 weeks old) were injected intravenously (IV) with $1 \times 10^5$ of CT-26 cells (murine colon carcinoma) in 0.2 ml PBS in the lateral tail vein on day 0. Treatment was with PROLEUKIN or IL-2/N88R at different doses (diluent: 5% dextrose in water (D5W)), or D5W, delivered IV, once daily for 8 days (QD×8) starting day 1 post-implantation. IL-2/N88R was prepared at room temperature by dilution into D5W using siliconized vials using a tuberculin syringe and dosed to animals within 2 hours of preparation. PROLEUKIN was prepared by adding 0.7 ml sterile water for injection (SWFI) to each vial (final concentration, 1.86 mg/ml). Dilutions were made as described for IL-2/N88R into D5W (Table 6). Animals were sacrificed at Day 11. Lungs were removed and weighed, rinsed in PBS, and tissue transferred to Bouin's solution. 24 hrs later, tissue was transferred to 10% formalin. The number of metastatic colonies in the lungs were counted under a dissecting microscope.

TABLE 6

Dose and groups in murine CT-26 tumor model study.

| Groups | n  | Treatment | Dose, mg/kg |
|--------|----|-----------|-------------|
| 1      | 14 | D5W       | NA          |
| 2      | 11 | PROLEUKIN | 3 mg/kg     |
| 3      | 11 | PROLEUKIN | 10 mg/kg    |
| 4      | 11 | IL-2/N88R | 1 mg/kg     |
| 5      | 12 | IL-2/N88R | 3 mg/kg     |
| 6      | 12 | IL-2/N88R | 10 mg/kg    |
| 7      | 12 | IL-2/N88R | 30 mg/kg    |
| 8      | 11 | IL-2/N88R | 60 mg/kg    |

Table 7 shows the number of metastasis counted in individual mice. Comparable efficacy was observed for both the IL-2/N88R and PROLEUKIN. At the high dose of IL-2/N88R (group 8, 60 mg/kg), all but one mouse had 12 metastasis or fewer; 3 of the mice exhibited no metastasis. This is in contrast to the highest dose of PROLEUKIN tested, where all surviving mice had 12 metastasis or greater.

TABLE 8

Survival of mice treated with IL-2/N88R or PROLEUKIN.

| Group | Day 0 | $7^4$ | 8 | 11 |
|-------|-------|-------|---|----|
| D5W[1] | 100.0% | 100.0% | 100.0% | 100.0% |
| Pro:3 mg/kg[2] | 100.0% | 100.0% | 100.0% | 100.0% |
| Pro:10 mg/kg[2] | 100.0% | 90.9% | 45.5% | 45.5% |
| IL-2/N88R:1 mg/kg[2] | 100.0% | 100.0% | 100.0% | 100.0% |
| IL-2/N88R:3 mg/kg[3] | 100.0% | 100.0% | 91.7% | 91.7% |
| IL-2/N88R:10 mg/kg[3] | 100.0% | 100.0% | 91.7% | 91.7% |
| IL-2/N88R:30 mg/kg[3] | 100.0% | 100.0% | 100.0% | 100.0% |
| IL-2/N88R:60 mg/kg[2] | 100.0% | 100.0% | 100.0% | 100.0% |

[1] n = 14 mice/group
[2] n = 11 mice/group
[3] n = 12 mice/group
[4] No deaths were observed prior to day 7.

PROLEUKIN treated animals in both groups were moribund. No morbidity was observed in any IL-2/N88R-treated animal.

In summary, these studies indicate that IL-2/N88R is as efficacious as PROLEUKIN at reducing tumor burden (as

TABLE 7

Individual metastases counts and means are listed.

| Group | Lung Metastases (counts for individual mice are listed) | | | | | | | | | | | | | Mean | SEM | P value (2-tailed) |
|-------|---|---|---|---|---|---|---|---|---|---|---|---|---|------|-----|-------------------|
| 1 | 0 | 129 | 183 | 179 | 155 | 165 | 200 | 152 | 148 | 158 | 200 | 194 | 165 | 125 | 154 | 13.42 | |
| 2 | 118 | 126 | 107 | 111 | 118 | 110 | 137 | 114 | 135 | 158 | 132 | | | | 124 | 4.61 | 0.07278 |
| 3 | 12 | 38 | 18 | 19 | 30 | | | | | | | | | | 23 | 4.66 | 0.00003 |
| 4 | 169 | 173 | 189 | 200 | 120 | 117 | 136 | 122 | 200 | 163 | 110 | | | | 154 | 10.41 | 0.97029 |
| 5 | 171 | 176 | 186 | 159 | 192 | 139 | 117 | 200 | 195 | 116 | 192 | | | | 168 | 9.31 | 0.43401 |
| 6 | 92 | 111 | 112 | 114 | 109 | 84 | 68 | 47 | 58 | 49 | 112 | | | | 87 | 8.16 | 0.00060 |
| 7 | 15 | 13 | 59 | 62 | 23 | 55 | 46 | 16 | 9 | 4 | 8 | 2 | | | 26 | 6.57 | 0.00000 |
| 8 | 7 | 0 | 3 | 2 | 4 | 9 | 7 | 0 | 12 | 55 | 0 | | | | 9 | 4.75 | 0.00000 |

Figure 19:
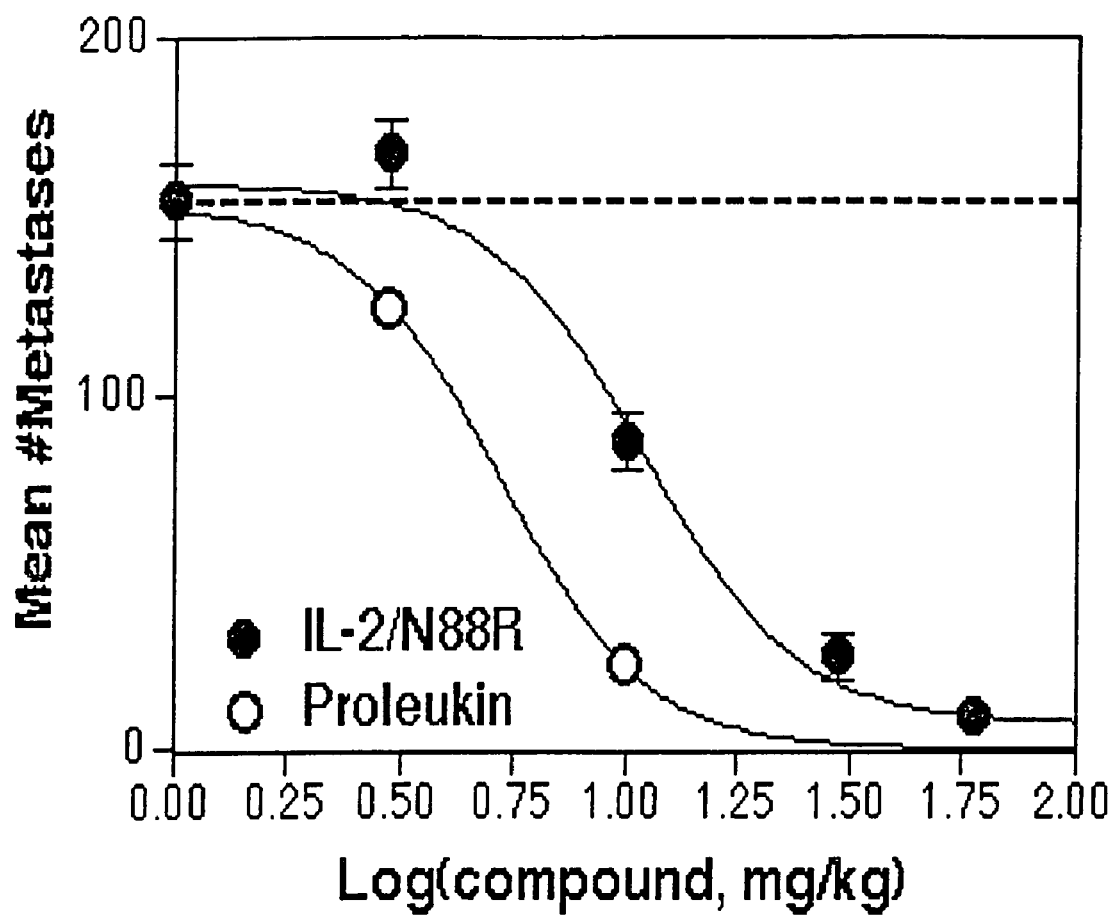

Significant (P<0.05) reduction in metastasis was seen in mice treated with IL-2/N88R at doses of 10, 30, and 60 mg/kg (groups 6,7, and 8, respectively), and in group treated with 10 mg/kg PROLEUKIN (group 3). These results are shown graphically in FIG. 19. Data is plotted using the log of the dose: for PROLEUKIN, doses were at 3 and 10 mg/kg; for IL-2/N88R, doses were at 1, 3 10, 30, and 60 mg/kg. Curve fitting using a non-linear equation (4-parameter fit) yielded $IC_{50}$ values of 5.2 mg/kg for PROLEUKIN, and 10.9 mg/kg for IL-2/N88R.

From the data in this experiment, the $IC_{50}$ with respect to reduction in metastasis number for IL-2/N88R was calculated to be 10.9 mg/kg (8.6–13.9 mg/kg at 95% confidence), and for PROLEUKIN to be 5.2 mg/kg (3.5–7.7 mg/kg at 95% confidence).

The survival of the mice are shown in Table 8. In the 10 mg/kg PROLEUKIN group, one (1) mouse died on Day 7, and an additional five (5) died on Day 8. One (1) mouse died on Day 8 in each of the groups treated with 3 or 10 mg/kg IL-2/N88R, and no deaths were observed in either 1, 30, or 60 mg/kg IL-2/N88R. Additionally, most mice treated with 3 mg/kg PROLEUKIN and all mice treated with 10 mg/kg PROLEUKIN were moribund; no morbidity was observed in IL-2/N88R-treated mice.

measured by lung metastasis count in the CT26 model). In addition, IL-2/N88R was shown to be substantially less toxic than PROLEUKIN.

Example 9

Development of Stable, High-Producing CHO Cell Lines that Express IL2N88R

Figure 20:
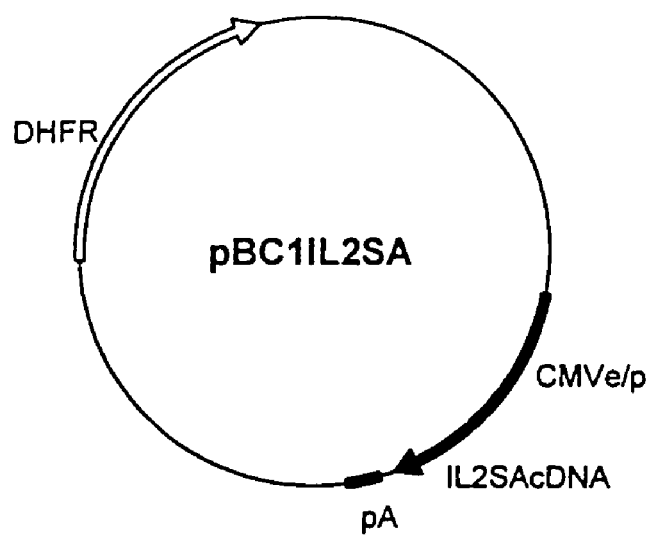

Stable production cell lines that secrete high quantities of the IL2N888R mutein were developed by transfecting CHO (dhfr-) cells with the expression vector shown in FIG. 20 (ATCC Deposit No. PTA-8). The individual elements of the IL2N88R, expression vector are shown in the plasmid map (FIG. 20). It shows CMVe/p=Cytomegalovirus early promoter; PA=SV40 polyadenylation signal sequence; and DHFR=dihydrofolate reductase expression cassette.

The vector was constructed using standard recombinant DNA techniques. See generally Sambrook et al., *Molecular Cloning*, 2d ed., 1989, Cold Spring Harbor Press; *Short Protocols in Molecular Biology*, 2d ed., 1992, John Wiley & Son; *Methods in Enzymology* vol. 185, Ed. Goeddel et al., Academic Press, Inc., London, 1991. The expression vector contains discrete expression cassettes for the IL2N88R gene and the amplifiable and selectable gene DHFR (dihydrofolate reductase). About 1×10⁶ CHO (Chinese hamster ovary) cells were transfected with 10 ug of pBC1IL2SA using Lipofectin reagents (Life Technology Inc., Bethesda, Md.) according to manufacturer's instructions. The cells were then selected in the presence of 50 nM methotrexate and grown in DME/F12 media (Life Technologies, Inc.) deficient in thymidine and hypoxanthine plus 5% dialyzed fetal bovine serum. Cell populations were screened for IL2N88R production with a commercial ELISA kit (R & D Systems). The high producing populations were further selected in media containing increasing concentrations of methotrexate (100 to 400 nM methotrexate) and screened for the production of IL2N88R. Limiting dilution cloning was then applied to derive clones with high and stable productivity. The cloning was done in the absence of methotrexate using standard tissue culture techniques.

Example 10

Serum Free Production of IL2N88R in a Perfusion Bioreactor

Continuous production of IL2N88R was done by continuous perfusion fermentation. A 19-liter Wheaton fermenter was inoculated with the stable CHO cell line of Example 9 at 2×10⁶ cells/ml and perfused at a medium exchange rate of 5 liters/day. The production medium was a DME/F12-based medium (Life Technologies, Inc., Rockville, Md.) supplemented with recombinant human insulin (10 ug/ml) (HUMULIN™, Eli Lilly, Inc., Indianapolis, Ind.) and FeSO4.EDTA (50 uM). The cell density was maintained at 4×10⁶ cells/ml. The average daily yield of the fermenter was ~200 mg/day. The production IL2N88R was stably maintained for 30 days.

Example 11

Purification of IL-2/N88R Produced in CHO Cells

The following procedure was applied to the perfusion eluate described above.

The perfusion medium was harvested and applied to an S-sepharose column. Muteins were then eluted with 20 mM ethanoloamine, pH 10.5, to wash the muteins off the column to produce the S-eluate.

Anion exchange was performed by passing the S eluate through a column of QAE Fast Flow™ (Pharmia) equilibrated with 10 mM Bicarbonate buffer at pH 10.5. Flow rate was maintained at 250 cm/hr. After washing to baseline IL-2SA was eluted with 20 mM phosphate pH 4.0.

Hydroxyapatite (HAP) chromatography was performed by passing the diluted QAE eluate (1:1 with WFI) across a column packed with ceramic hydroxyapatite (Type II, Bio-Rad, Hercules, Calif.) equilibrated with 0.10 mM Phosphate at pH 7.0. Flow rate was maintained at 250 cm hr-1. After washing to baseline IL2SA was eluted with 100 mM Phosphate at pH 7.0.

The hydroxyapatite eluate was ultrafiltered to 300 ml volume with a Millipore Pelicon-2 unit fitted with three PES 5K cartridges (Millipore Corporation, Bedford, Mass.).

The ultrafiltered HAP eluate was further purified by passage across a S100HR (Pharmacia) size exclusion column at 35 cm/hr. The column was equilibrated with 10 mM Phosphate and 150 mM NaCl pH 7.0.

The Gel Filtration pool was diluted with WFI to attain a conductivity of 4.0 mMhos/cm and was reapplied to S-Sepharose under conditions previously described. IL2SA was eluted with 10 mM Phosphate buffer with 1 Molar NaCl at pH 7.0.

Final Cation exchange pool was dialysed against Phosphate Buffered Saline (PBS) overnight and the diluted with sterile PBS to a concentration of 6 mgs/ml. The final diluted pool was then sterile filtered, aliquotted and then frozen at −70° C. Total recovery was 65%.

Other embodiments of the invention will become apparent to one of skill in the art. This invention teaches how to obtain muteins not specifically described herein but which cause T cell activation as evidenced by PHA-blast proliferation, and reduced NK-cell proliferation, and thereby those muteins come within the spirit and scope of the invention. The concept and experimental approach described herein should be applicable to other cytokines utilizing heterologous multimeric receptor systems, in particular related cytokines IL-7, IL-9 and IL-1 5, IL-10, interferon α, and interferon γ.

SEQUENCES

The following sequences are contained within this application:

SEQ ID NO: 1: hIL-2 (amino acid)

SEQ ID NO: 2: hIL-2 (cDNA)

SEQ ID NO: 3: 5' PCR Primer, IL-2

SEQ ID NO: 4: 3' PCR Primer, IL-2

SEQ ID NO: 5: Mutagenesis Primer for IL-2 expression vector

SEQ ID NO: 6: Mutagenesis Primer for D20X mutations

SEQ ID NO: 7: Mutagenesis Primer for N88X mutations

SEQ ID NO: 8: Mutagenesis Primer for Q126X mutations

---

We claim:

1. An isolated polynucleotide comprising a nucleotide sequence encoding a human IL-2 mutein with a substitution at amino acid position 88 relative to wild type IL-2, said wild type IL-2 consisting of the amino acid sequence set forth in SEQ ID NO:1.

2. A prokaryotic host cell transformed with the polynucleotide of claim 1.

3. An isolated vector comprising the polynucleotide of claim 1.

* * * * *

SEQUENCE LISTING

```
<160> NUMBER OF SEQ ID NOS: 8

<210> SEQ ID NO 1
<211> LENGTH: 133
<212> TYPE: PRT
<213> ORGANISM: Homo Sapiens

<400> SEQUENCE: 1

Ala Pro Thr Ser Ser Ser Thr Lys Lys Thr Gln Leu Gln Leu Glu His
 1               5                  10                  15
```

```
Leu Leu Leu Asp Leu Gln Met Ile Leu Asn Gly Ile Asn Asn Tyr Lys
         20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
             100                 105                 110

Thr Ile Val Glu Phe Leu Asn Arg Trp Ile Thr Phe Cys Gln Ser Ile
             115                 120                 125

Ile Ser Thr Leu Thr
             130

<210> SEQ ID NO 2
<211> LENGTH: 465
<212> TYPE: DNA
<213> ORGANISM: Homo Sapiens

<400> SEQUENCE: 2
atgtacagga tgcaactcct gtcttgcatt gcactaagtc ttgcacttgt cacaaacagt      60
gcacctactt caagttctac aaagaaaaca cagctacaac tggagcattt actgctggat     120
ttacagatga ttttgaatgg aattaataat acaagaatc ccaaactcac caggatgctc     180
acatttaagt tttacatgcc caagaaggcc acagaactga acatcttca gtgtctagaa     240 gaagaactca aacctctgga ggaagtgcta aatttagctc aaagcaaaaa ctttcactta     300
agacccaggg acttaatcag caatatcaac gtaatagttc tggaactaaa gggatctgaa     360
acaacattca tgtgtgaata tgctgatgag acagcaacca ttgtagaatt tctgaacaga     420
tggattacct tttgtcaaag catcatctca acactgactt gataa                    465

<210> SEQ ID NO 3
<211> LENGTH: 30
<212> TYPE: DNA
<213> ORGANISM: Homo Sapiens

<400> SEQUENCE: 3
cctcaactcc tgaattcatg tacaggatgc                                      30

<210> SEQ ID NO 4
<211> LENGTH: 31
<212> TYPE: DNA
<213> ORGANISM: Homo Sapiens

<400> SEQUENCE: 4
ggaagcggat ccttatcaag tcagtgttga g                                    31

<210> SEQ ID NO 5
<211> LENGTH: 36
<212> TYPE: DNA
<213> ORGANISM: Homo Sapiens

<400> SEQUENCE: 5
gcacttgtca caaacaccat ggcacctact tcaagt                               36
```

```
<210> SEQ ID NO 6
<211> LENGTH: 28
<212> TYPE: DNA
<213> ORGANISM: Homo Sapiens
<220> FEATURE:
<221> NAME/KEY: misc_feature
<222> LOCATION: 17, 18, 19
<223> OTHER INFORMATION: n = a, t, c, or g

<400> SEQUENCE: 6
ggagcattta ctgctgnnnt tacagatg                                      28

<210> SEQ ID NO 7
<211> LENGTH: 30
<212> TYPE: DNA
<213> ORGANISM: Homo Sapiens
<220> FEATURE:
<221> NAME/KEY: misc_feature
<222> LOCATION: 15, 16, 17
<223> OTHER INFORMATION: n = a, t, c, or g

<400> SEQUENCE: 7
gggacttaat cagcnnnatc aacgtaatag                                    30

<210> SEQ ID NO 8
<211> LENGTH: 28
<212> TYPE: DNA
<213> ORGANISM: Homo Sapiens
<220> FEATURE:
<221> NAME/KEY: misc_feature
<222> LOCATION: 15, 16, 17
<223> OTHER INFORMATION: n = a, t, c, or g

<400> SEQUENCE: 8
ggattacctt ttgtnnnagc atcatctc                                      28
```